(12) United States Patent
Ooga et al.

(10) Patent No.: US 10,249,043 B2
(45) Date of Patent: Apr. 2, 2019

(54) BLOOD VESSEL ANALYSIS APPARATUS, MEDICAL IMAGE DIAGNOSIS APPARATUS, AND BLOOD VESSEL ANALYSIS METHOD

(71) Applicant: Toshiba Medical Systems Corporation, Otawara-shi (JP)

(72) Inventors: Junichiro Ooga, Kawasaki (JP); Kenji Hirohata, Tokyo (JP); Shigeo Kaminaga, Otawara (JP); Yasuko Fujisawa, Nasushiobara (JP); Satoshi Wakai, Nasushiobara (JP); Kazumasa Arakita, Nasushiobara (JP); Takuma Igarashi, Nasushiobara (JP); Hideaki Ishii, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 15/896,282

(22) Filed: Feb. 14, 2018

(65) Prior Publication Data

US 2018/0174297 A1    Jun. 21, 2018

Related U.S. Application Data

(63) Continuation of application No. 14/731,908, filed on Jun. 5, 2015, now Pat. No. 9,928,593, which is a
(Continued)

(30) Foreign Application Priority Data

Dec. 7, 2012    (JP) .................................. 2012-268714

(51) Int. Cl.
*G06K 9/00*    (2006.01)
*A61B 6/00*    (2006.01)
(Continued)

(52) U.S. Cl.
CPC .......... *G06T 7/0016* (2013.01); *A61B 5/0044* (2013.01); *A61B 6/03* (2013.01);
(Continued)

(58) Field of Classification Search
USPC ........ 382/100, 103, 106–107, 128–134, 154, 382/162, 168, 173, 181, 199, 219, 232,
(Continued)

(56) References Cited

U.S. PATENT DOCUMENTS 8,068,894 B2 * 11/2011 Huizenga ............... A61B 5/055
382/276
8,315,813 B2 * 11/2012 Taylor ................. A61B 5/02007
702/19
(Continued)

FOREIGN PATENT DOCUMENTS

CN    103270513 A    8/2013
CN    104736061 A    6/2015
(Continued)

OTHER PUBLICATIONS

English Translation of the International Search Report dated Feb. 10, 2014 in PCT/JP2013/082872 filed Dec. 6, 2013.
(Continued)

*Primary Examiner* — Seyed H Azarian
(74) *Attorney, Agent, or Firm* — Oblon, McClelland, Maier & Neustadt, L.L.P.

(57) ABSTRACT

According to one embodiment, a structuring circuitry temporarily structures a dynamical model of analysis processing based on the time-series medical image. The identification circuitry identifies a latent variable of the dynamical model so that at least one of a prediction value of a blood vessel morphology and a prediction value of a bloodstream based on the temporarily structured dynamical model is in conformity with at least one of an observation value of the blood
(Continued)

vessel morphology and an observation value of the bloodstream measured in advance. The analysis circuitry analyzes the dynamical model to which the identified latent variable is allocated.

19 Claims, 15 Drawing Sheets

Related U.S. Application Data continuation of application No. PCT/JP2013/082872, filed on Dec. 6, 2013.

(51) Int. Cl.
- *G06T 7/00* (2017.01)
- *A61B 6/03* (2006.01)
- *A61B 5/00* (2006.01)
- *G06T 7/246* (2017.01)

(52) U.S. Cl.
CPC .............. *A61B 6/486* (2013.01); *A61B 6/503* (2013.01); *A61B 6/5217* (2013.01); *G06T 7/0012* (2013.01); *G06T 7/246* (2017.01); *G06T 7/251* (2017.01); *A61B 6/481* (2013.01); *A61B 6/504* (2013.01); *G06T 2207/10016* (2013.01); *G06T 2207/10076* (2013.01); *G06T 2207/10081* (2013.01); *G06T 2207/20076* (2013.01); *G06T 2207/30048* (2013.01); *G06T 2207/30101* (2013.01); *G06T 2207/30104* (2013.01)

(58) Field of Classification Search
USPC ....... 382/254, 274, 276, 288, 291, 305, 286; 378/4, 21, 23; 703/11; 424/1.11
See application file for complete search history.

(56) References Cited

U.S. PATENT DOCUMENTS

| | | |
|---|---|---|
| 2003/0233039 A1 | 12/2003 | Shao et al. |
| 2008/0249743 A1 | 10/2008 | Hirohata et al. |
| 2010/0014739 A1* | 1/2010 | Kiraly .................... G06K 9/342 382/131 |
| 2010/0017171 A1 | 1/2010 | Spilker et al. |
| 2011/0235883 A1 | 9/2011 | Nakagawa et al. |
| 2012/0041739 A1* | 2/2012 | Taylor ................ A61B 5/02007 703/11 |
| 2012/0259608 A1 | 10/2012 | Spilker et al. |
| 2013/0230454 A1* | 9/2013 | Gardner ................. A61K 38/18 424/1.11 |

FOREIGN PATENT DOCUMENTS

| | | |
|---|---|---|
| JP | 2005-528974 A | 9/2005 |
| JP | 2008-241432 A | 10/2008 |
| JP | 2011-200549 A | 10/2011 |
| WO | WO 2012/021307 A2 | 2/2012 |

OTHER PUBLICATIONS

Hiroshi Ryu. "Junkankei ni Okeru Multiscale Keisan Biomechanics", Journal of the Society of Biomechanisms, vol. 28, No. 4, 2004. pp. 173-178.

International Written Opinion dated Feb. 10, 2014 in PCT/JP2013/082872 filed Dec. 6, 2013 with English translation.

Yoshimasa Kadooka, "Tailor-made medicine pioneered by heart simulator" International Telecommunication Union Journal, vol. 41, No. 6, Jun. 2011, pp. 41-44.

Chinese Office Action dated Apr. 5, 2017, issued in Chinese Patent Application No. 201380063359.7 (with English translation).

\* cited by examiner

| ID | Property | CT value range | Material model parameter |
|---|---|---|---|
| 1 | Normal blood vessel wall | −100~+100 | Parameter A |
| 2 | Atherosclerotic plaque | +100~+300 | Parameter B |
| 3 | Calcified plaque | +300~+700 | Parameter C |

● : Node where constraint condition is allocated
○ : Node where constraint condition is not allocated

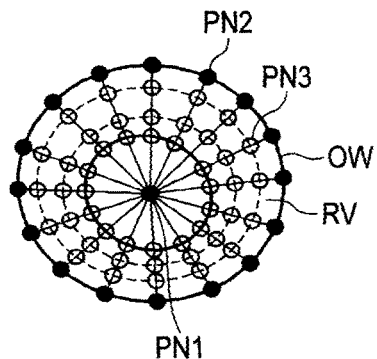

Case where constraint is given only to external surface with forcible displacement history
Latent variable (boundary condition, material model, and load condition are identified)

F I G. 14A

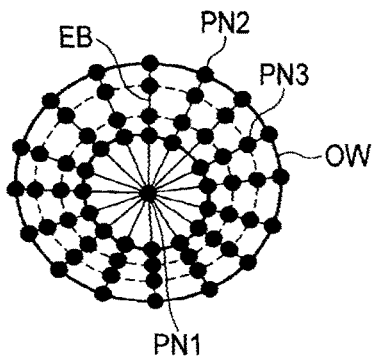

Case where constraint is given also to lumen side with forcible displacement history
Latent variable (boundary condition, material model, and load condition are identified)

F I G. 14B

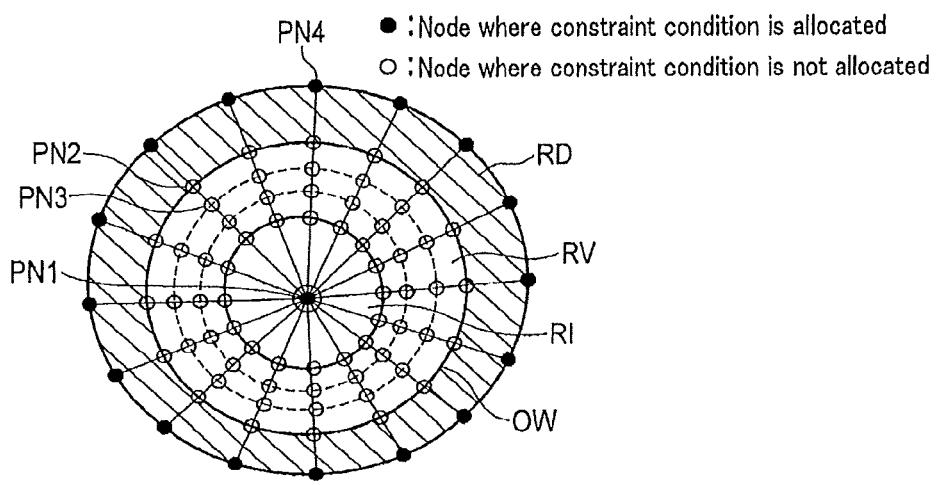
F I G. 15
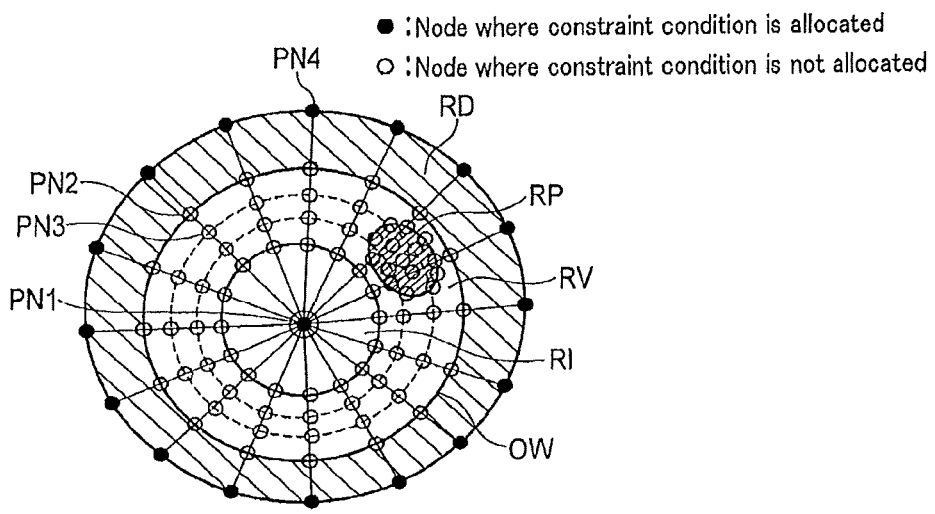
F I G. 16

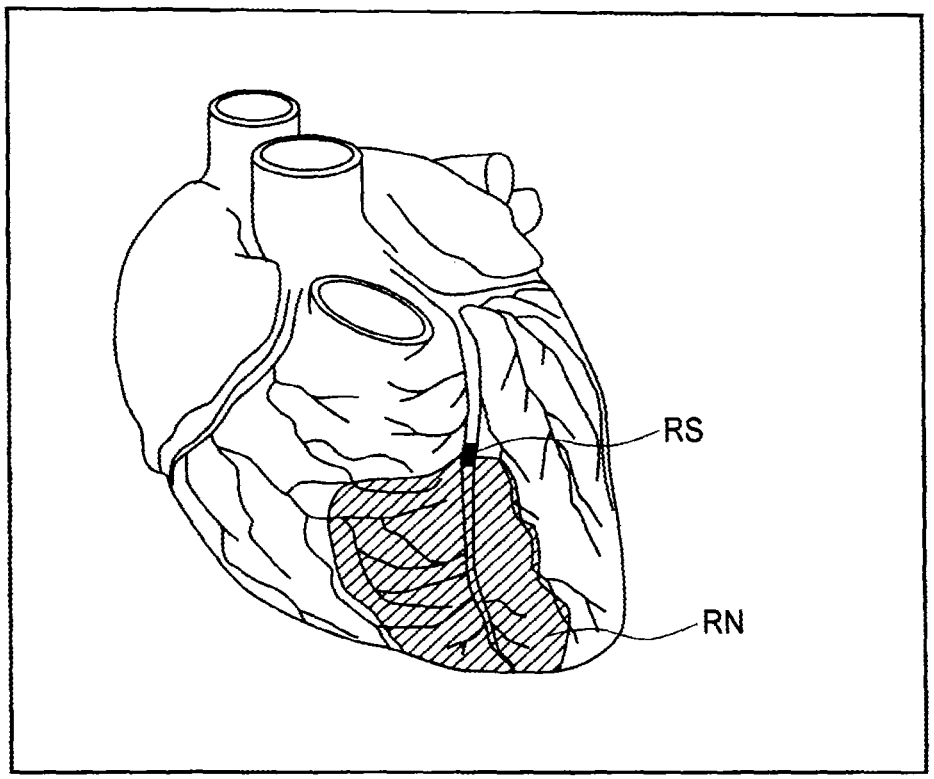
F I G. 17A

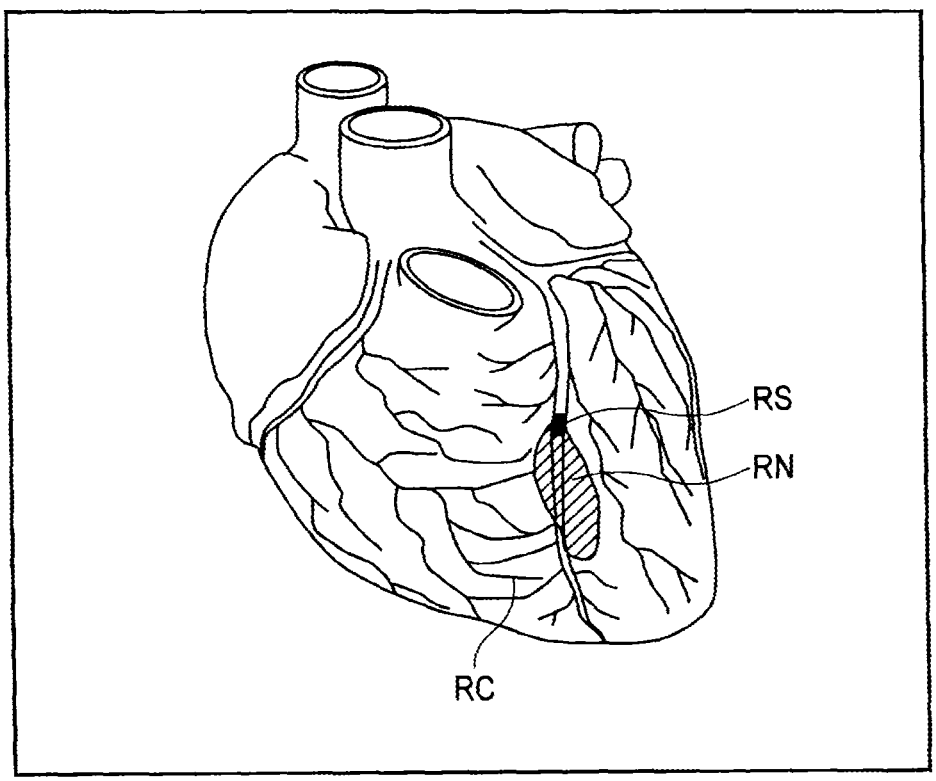
F I G. 17B

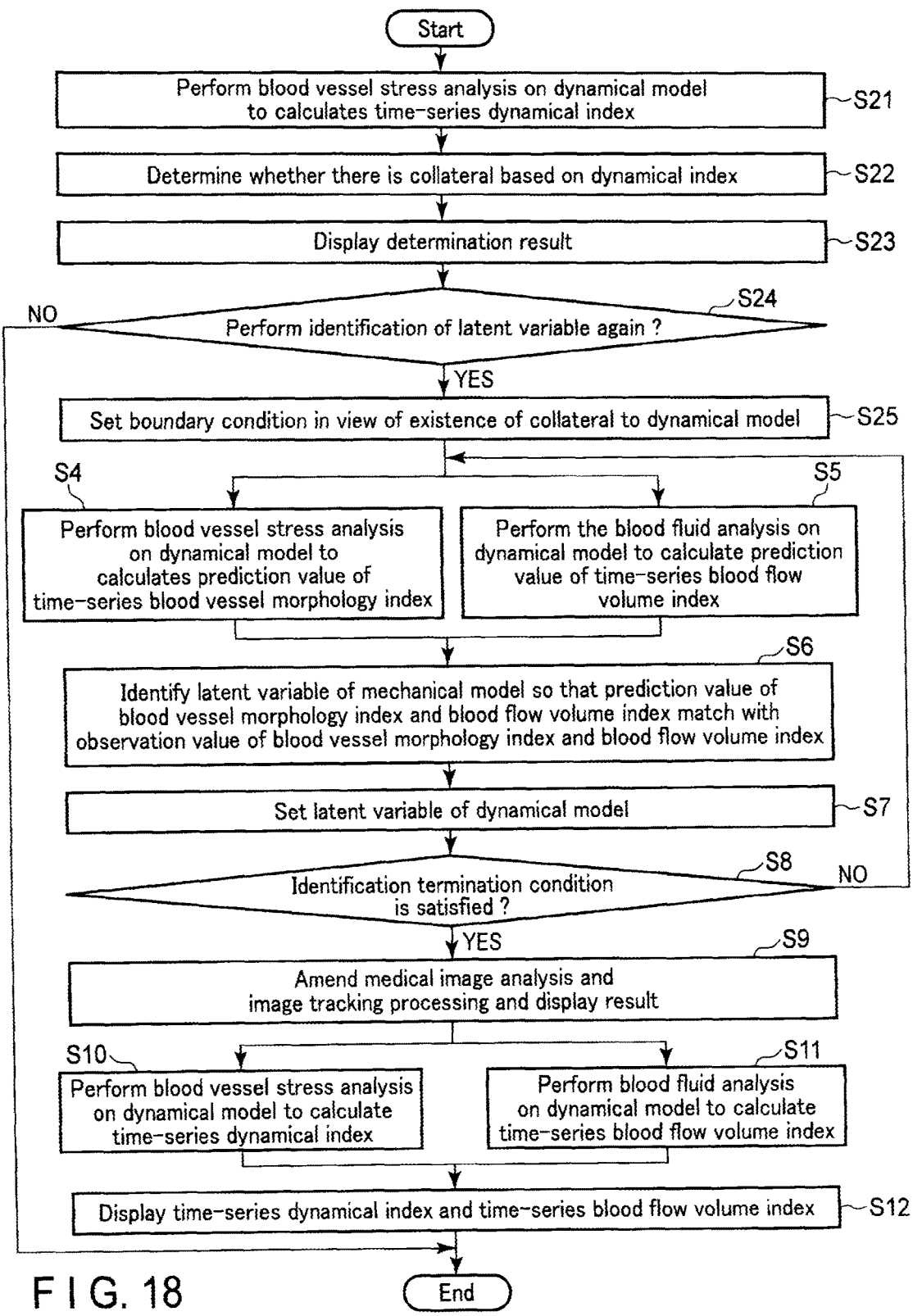
F I G. 18

BLOOD VESSEL ANALYSIS APPARATUS, MEDICAL IMAGE DIAGNOSIS APPARATUS, AND BLOOD VESSEL ANALYSIS METHOD

CROSS-REFERENCE TO RELATED APPLICATIONS

This application is a Continuation Application of U.S. patent application Ser. No. 14/731,908, filed on Jun. 5, 2015, which is a Continuation of PCT Application No. PCT/JP2013/082872, filed on Dec. 6, 2013, which is based upon and claims the benefit of priority from the Japanese Patent Application No. 2012-268714, filed on Dec. 7, 2012; the entire contents of each of which are incorporated herein by reference.

FIELD

Embodiment described herein relate generally to a blood vessel analysis apparatus, a medical image diagnosis apparatus, and a blood vessel analysis method.

BACKGROUND

It is desired to develop a noninvasive or minimally invasive technique for preventing and diagnosing stenosis of a coronary artery causing heart disease which is one of three major diseases, cerebral aneurysm, or stenosis caused by a plaque of a carotid artery which may be a premonition thereof.

Stenosis of a coronary artery is a serious pathologic change that may lead to ischemic heart disease. A diagnosis of stenosis of a coronary artery is mainly Coronary Angiography (CAG) using a catheter. A diagnosis index of an organic pathologic change of a coronary artery includes Fractional Flow Reserve (FFR). The FFR is defined as a ratio of the maximum coronary blood flow where stenosis exists with respect to the maximum coronary blood flow where stenosis does not exist. The FFR is substantially the same as the ratio of a stenosis distal portion coronary internal pressure with respect to a stenosis proximal portion coronary internal pressure. The FFR is measured by a pressure sensor provided at a catheter distal end. More specifically, a catheter operation is required to measure the FFR.

When the analysis of stenosis of the coronary artery can be performed with a heart CT, this is minimally invasive, and can reduce the burden imposed on the patient and save the medical cost as compared with the measurement of the FFR with the catheter operation. However, in the heart CT, only the index based on the size of a plaque region or a thrombus region included in a CT image can be measured in a minimally invasive manner. If a pressure difference and the like before and after the thrombus can be measured based on the CT image by structural fluid analysis, the effect exerted by the thrombus (or plaque) is expected to be quantified.

Medical imaging techniques such as ultra-fast CT, cine angiography, MRI (magnetic resonance image method), ultrasonic imaging method, SPECT (single photon emission tomography), PET (positron emission tomography), and the like have been developed in terms of clinical aspect as a dynamic evaluation of coronary circulation, and are used for evaluation of diagnosis and treatment methods.

However, it is difficult for a medical image diagnosis apparatus to accurately recognize coronary microvessels. Even if a blood vessel shape is clear, a medical image may include noises, and the threshold value setting at the boundary of a living tissue may be ambiguous. As described above, a blood vessel shape obtained by the medical image diagnosis apparatus involves uncertainty.

When a medical image diagnosis apparatus is utilized in a clinical application, analysis is often performed on the target of only a thick region of coronary artery from the origin of the aorta at the upstream of the coronary microvessels. Since the bloodstream of the coronary artery is also greatly affected by the tonus of the coronary microvessels, it is the problem to appropriately set boundary conditions of fluid analysis such as the volume of flow or pressure at the exit of the coronary artery of the thick region or the rate of change thereof. The bloodstream of the coronary artery receives mechanical factors of pulsation of the heart (overall movement caused by pulsation, and forced displacement or external force due to local expansion and contraction, twisting, and shearing deformation). With the fluid analysis alone, the effect of the mechanical factors such as pulsation of the heart cannot be taken into consideration, and therefore, the volume of flow distribution of the bloodstream and the internal pressure distribution cannot be accurately measured. On the other hand, a structure-fluid interaction analysis is also carried out on the heart and the blood vessel system captured in an image in view of the effects of the mechanical factors. However, even when the structure-fluid interaction analysis is performed, it is often difficult to correctly set the material model of the blood vessel and the plaque and the boundary condition at the entrance and the exit of the blood vessel in the fluid analysis of the blood (including contrast agent). When there is a microvessel that is not captured in the image, the effect of the microvessel given to the bloodstream cannot be taken into consideration. For this reason, the analysis result of the structure-fluid interaction analysis may not be reproducing actual bloodstream and blood vessel deformation. In a case where the boundary condition, the load condition, and the material model are not appropriate, or in a case where the blood vessel involves great movement, there may be a problem in the convergence and the analysis stability. As described above, in conventional structural fluid analysis of blood vessels, it may be required to have large analysis resources and it may take an analysis time, or the error of the analysis result may increase, and therefore, there may be a problem in the utilization in actual clinical scenes.

BRIEF DESCRIPTION OF THE DRAWING

FIG. 14A is a figure illustrating another example of allocation of a forced displacement history according to the dynamical model structuring circuitry of FIG. 4.

FIG. 14B is a figure illustrating another example of allocation of a forced displacement history according to the dynamical model structuring circuitry of FIG. 4.

FIG. 15 is a figure illustrating another example of allocation of a forced displacement history according to the dynamical model structuring circuitry of FIG. 4.

FIG. 16 is a figure illustrating another example of allocation of a forced displacement history according to the dynamical model structuring circuitry of FIG. 4.

FIG. 17A is a schematic diagram of a heart where any collateral does not exist.

FIG. 17B is a schematic diagram of a heart where collateral exists.

FIG. 18 is a figure illustrating a typical flow of processing performed under control of the system control circuitry according to an application example of the present embodiment.

DETAILED DESCRIPTION

In general, according to one embodiment, a blood vessel analysis apparatus includes a storage, a structuring circuitry, an identification circuitry, and an analysis circuitry. The storage is configured to store data of a time-series medical image of a blood vessel of a subject. The structuring circuitry is configured to temporarily structure a dynamical model of analysis processing based on the time-series medical image. The identification circuitry is configured to identify a latent variable of the dynamical model so that at least one of a prediction value of a blood vessel morphology and a prediction value of a bloodstream based on the temporarily structured dynamical model is in conformity with at least one of an observation value of the blood vessel morphology and an observation value of the bloodstream measured in advance. The analysis circuitry is configured to analyze the dynamical model to which the identified latent variable is allocated.

A blood vessel analysis apparatus, a medical image diagnosis apparatus, and a blood vessel analysis method according to the present embodiment will be hereinafter explained with reference to drawings.

A blood vessel analysis apparatus according to the present embodiment is a computer apparatus for performing structural fluid analysis on a blood vessel region included in a medical image generated by a medical image diagnosis apparatus. The blood vessel analysis apparatus according to the present embodiment may be incorporated into a medical image diagnosis apparatus, or may be a computer apparatus such as a work station provided separately from the medical image diagnosis apparatus. In order to explain in a specific manner, the blood vessel analysis apparatus according to the present embodiment is considered to be incorporated into the medical image diagnosis apparatus in the explanation below.

The medical image diagnosis apparatus according to the present embodiment can be applied to any type of image diagnosis apparatus provided with an imaging mechanism scanning a subject. For example, an X-ray computed tomography apparatus (X-ray CT apparatus), a magnetic resonance diagnosis apparatus, ultrasonic diagnosis apparatus, SPECT apparatus, PET apparatus, radiological treatment apparatus, and the like can be used as necessary as the medical image diagnosis apparatus according to the present embodiment. In order to explain in a specific manner, the medical image diagnosis apparatus according to the present embodiment is considered to be an X-ray computed tomography apparatus s in the explanation below.

Figure 1:
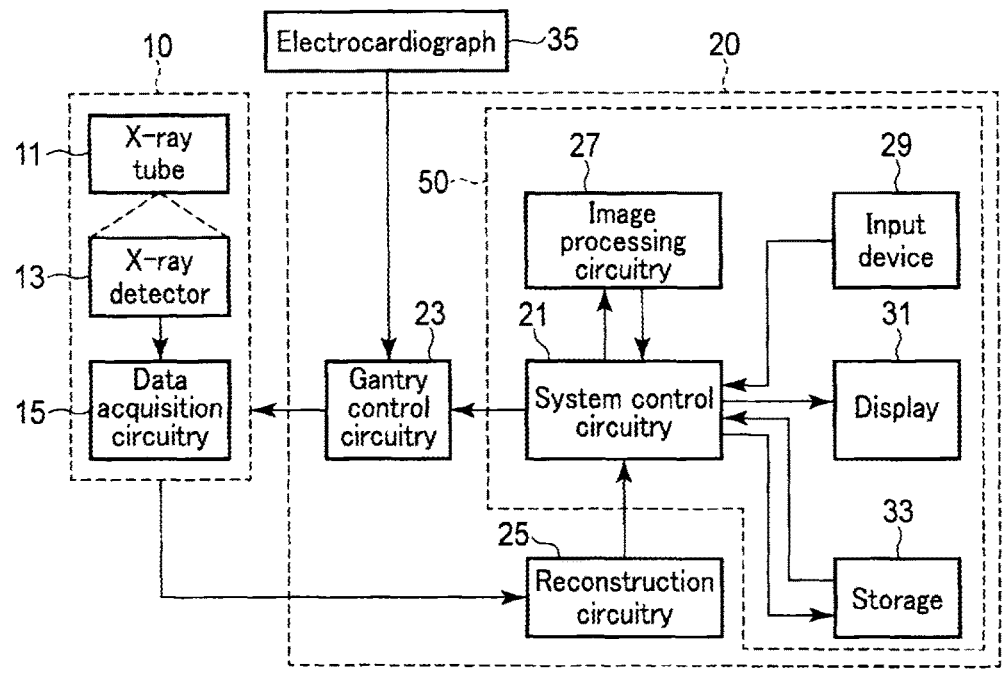
FIG. 1 is a figure illustrating a schematic block configuration of a medical image diagnosis apparatus (X-ray computed tomography apparatus) according to the present embodiment.

FIG. 1 is a schematic block configuration diagram illustrating the medical image diagnosis apparatus according to the present embodiment (X-ray computed tomography apparatus). As shown in FIG. 1, the X-ray computed tomography apparatus includes a CT gantry 10 and a console 20. The CT gantry 10 scans an imaging part of a subject using an X-ray in accordance with the control of the gantry control circuitry 23 of the console 20. The imaging part is, for example, a heart. The CT gantry 10 includes an X-ray tube 11, an X-ray detector 13, and a data acquisition circuitry 15. The X-ray tube 11 and the X-ray detector 13 are provided on the CT gantry 10 so as to be able to rotate about a rotation axis. The X-ray tube 11 emits an X-ray onto a subject in which a contrast agent is injected. The X-ray detector 13 detects the X-ray generated from the X-ray tube 11 and transmitted through the subject, and generates an electric signal in accordance with the intensity of the detected X-ray. The data acquisition circuitry 15 reads the electric signal from the X-ray detector 13 and converts the electric signal into digital data. A set of digital data for each view is referred to as a raw data set. A time-series raw data set of multiple scan times are transmitted by a non-contact data transmission apparatus (not shown) to the console 20.

The console 20 has a system control circuitry 21 as a center, and includes a gantry control circuitry 23, a reconstruction circuitry 25, an image processing circuitry 27, an input device 29, a display 31, and a storage 33. The console 20 is connected to an electrocardiograph 35. The electrocardiograph 35 generates cardiac beat information about the subject, and provides the cardiac beat information to the gantry control circuitry 23 of the console 20.

The gantry control circuitry 23 controls each apparatus in the console 20 in accordance with a scan condition set with the input device 29 by the user. The gantry control circuitry 23 executes scan in synchronization with the cardiac beat information provided by the electrocardiograph 35.

The reconstruction circuitry 25 generates data of a CT image of a subject based on a raw data set. More specifically, first, the reconstruction circuitry 25 generates a projection data set by preprocessing the raw data set. The preprocessing includes logarithmic transformation, non-uniform correction, calibration correction, and the like. Subsequently, the reconstruction circuitry 25 generates data of a CT image by applying image reconstruction processing to the projection data set. Existing algorithms such as analytic image reconstruction methods such as filtered back projection (FBP) method and successive approximation image reconstruction such as maximum likelihood expectation maximization (ML-EM) method and ordered subset expectation maximization (OS-EM) method can be applied as the image reconstruction algorithm. In the present embodiment, the reconstruction circuitry 25 generates time-series data of CT images based on time-series projection data set. The CT image includes pixel regions of blood vessels imaged with the contrast agent (hereinafter referred to as blood vessel regions). It should be noted that the CT image may be slice data representing two-dimensional space distribution of CT values, or may be volume data representing three-dimensional space distribution of CT values. Hereinafter, a CT image is considered to be volume data. The data of the time-series CT image are stored in the storage 33.

The image processing circuitry 27 executes structural fluid analysis by structuring a dynamical model based on the time-series CT images. The details of the processing of the image processing circuitry 27 will be explained later.

The input device 29 receives various kinds of commands and information inputs from the user. A keyboard, a mouse, a switch, and the like can be used as the input device 29.

The display 31 displays various kinds of information such as a CT image, a structural fluid analysis result, and the like. For example, a CRT display, a liquid crystal display, an organic EL display, a plasma display and the like can be used as the display 31 as necessary.

The storage 33 is constituted by various kinds of storage media such as a hard disk apparatus. The storage 33 stores various kinds of data such as time-series projection data, time-series CT image data, and the like. For example, the storage 33 stores time-series CT image data in a medical image file format based on digital imaging and communications in medicine (DICOM) specification. The storage 33 may store medical data collected by an external device in association with time-series CT image data in a medical image file.

The system control circuitry 21 includes a central processing unit (CPU), region only memory (ROM), a random access memory (RAM). The system control circuitry 21 functions as the center of the X-ray computed tomography apparatus. The system control circuitry 21 executes the blood vessel structure analysis processing according to the present embodiment by executing the blood vessel analysis program stored in the ROM and the RAM.

It should be noted that the system control circuitry 21, the image processing circuitry 27, the input device 29, the display 31, and the storage 33 constitute the blood vessel analysis apparatus 50. Like the present embodiment, the blood vessel analysis apparatus 50 may be incorporated into the medical image diagnosis apparatus (X-ray computed tomography apparatus), or may be a computer apparatus provided separately from the medical image diagnosis apparatus. The blood vessel analysis apparatus 50 is provided separately from the medical image diagnosis apparatus, the blood vessel analysis apparatus 50 may collect medical data such as time-series CT images via a network from the medical image diagnosis apparatus and a picture archiving and communication systems (PACS).

Subsequently, an example of operation of the present embodiment will be explained in details. The blood vessel analysis apparatus, medical image diagnosis apparatus, blood vessel analysis method, and the blood vessel analysis program according to the present embodiment can adopt, as the analysis target, blood vessels in any portion of the human body such as a heart blood vessel, a carotid artery, and a cerebral artery. However, in order to explain in a specific manner, analysis target according to the present embodiment is considered to be a blood vessel in the heart in the explanation below.

Examples of blood vessels of the heart include a coronary artery and an aorta. The coronary artery starts from the coronary artery origin of the aorta, runs on the cardiac muscle surface and enter into the endocardium side from the epicardium side. The coronary artery branches into numerous number of capillaries at the endocardium of the cardiac muscle. After the coronary artery branches into numerous number of capillaries, the numerous number of capillaries are united again to form a great cardiac vein and connected to the coronary sinus. Unlike other organs, the coronary vascular system is characterized in that the perfusion is to be ensured in dynamics change of contraction and relaxation of the cardiac muscle.

The blood vessel analysis apparatus 50 according to the present embodiment structures the dynamical model based on the time-series CT images, and executes the structural fluid analysis on the blood vessel of the heart by using the dynamical model, and accurately calculates the dynamics index and the blood flow volume index in the blood vessel. Hereinafter, the blood flow volume index will be referred to as a bloodstream index. In order to accurately calculate the dynamics index and the bloodstream index, it is necessary to allocate a highly accurate latent variable to the dynamical model. When the blood vessel analysis apparatus 50 structures the dynamical model, the blood vessel analysis apparatus 50 statistically identifies a latent variable by performing inverse analysis on the initial dynamical model. Therefore, the blood vessel analysis apparatus 50 can accurately determine the latent variable. The dynamics index means the dynamics index about the blood vessel wall. The dynamics index about the blood vessel wall is classified into, for example, an index of displacement of a blood vessel wall, an index of stress and distortion applied to a blood vessel wall, an index of internal pressure distribution applied to an intravascular lumen, an index of material characteristics representing the hardness of the blood vessel, and the like. The index of material characteristics representing the hardness of the blood vessel includes, e.g., an average inclination of a curved line representing a relationship of stress and distortion of a blood vessel tissue. The bloodstream index means an index of hemodynamics about blood flowing in a blood vessel. Examples of bloodstream indexes include the volume of flow of blood, the flow rate of blood, viscosity of blood, and the like.

The latent variable includes, for example, at least one of a parameter of a material model such as a material constitutive equation of blood vessel or a material constitutive equation of blood (for example, Young's modulus, Poisson's ratio, and the like), a load condition parameter such as an internal pressure distribution applied to an intravascular lumen, a boundary condition parameter of structure analysis and fluid analysis, and a variation distribution parameter related to uncertainty of a time-series morphology index and shape deformation index. In this case, a variation distribution parameter related to uncertainty of time-series morphology index and shape deformation index is such that various kinds of uncertainties are expressed as probability distributions in view of the fact that medical image data include variation distribution caused by noise of each CT value, probability distribution caused by ambiguity of a boundary threshold value of a living tissue, and the like. Examples of various kinds of uncertainties include uncertainty in a space coordinate of boundary coordinates of blood vessel tissue and blood and feature points (such as a blood vessel branching portion, a contrast agent distribution arrangement, and the like), uncertainty of a geometric structure parameter (lumen radius and the like in a cross section perpendicular to a center line), and uncertainty of a medical image data itself (such as a CT value, a boundary threshold value, and the like).

The dynamical model is a numerical model expressing behavior of a blood vessel and blood. The dynamical model has different types according to schemes of structural fluid analysis. For example, the dynamical model is classified into continuum dynamical model and simplified dynamical model. The continuum dynamical model is used for, for example, finite element method (FEM) and boundary element method. The simplified dynamical model is classified into, for example, a material dynamical model based on material dynamics and a fluid dynamical model based on flow studies. Unless otherwise specified in the following explanation, the type of the dynamical model is not particularly limited. The initial dynamical model is considered to mean a dynamical model allocated with a sampling set about parameters of latent variables that can be obtained from a variable range and probability distribution of latent variables (a set of combination of parameters).

Figure 2:
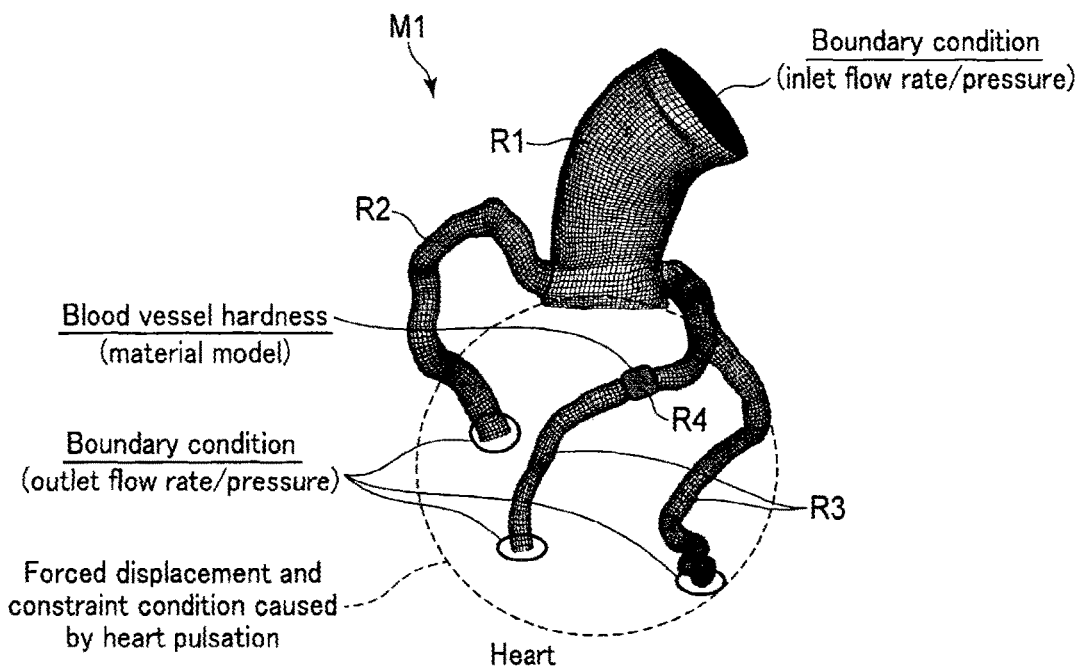
FIG. 2 is a figure illustrating an example of a dynamical model of a target region of a structural fluid analysis according to the present embodiment.

FIG. 2 is a figure illustrating an example of a dynamical model M1 of a target region of structural fluid analysis (hereinafter referred to as an analysis target region). As shown in FIG. 2, the dynamical model M1 includes an aorta region R1, a right coronary artery region R2, and a left coronary artery region R3. The blood flows from the aorta to the right coronary artery or the left coronary artery.

As shown in FIG. 2, in the dynamical model M1, the end at the side of the origin of the aorta is set as the entrance of the bloodstream, and the end of the right coronary artery region and the end of the left coronary artery region are set as the exit of the bloodstream. A boundary condition is set at each of the entrance and the exit. The boundary condition about the entrance includes, for example, the flow rate of the bloodstream, or the pressure generated by the bloodstream at the entrance, or the rate of change thereof. The boundary condition about the exit includes, for example, the flow rate of the bloodstream, or the pressure generated by the bloodstream at the exit, or the rate of change thereof. The deformation of the aorta, the right coronary artery, and the left coronary artery depends on various factors such as mechanical action to the blood vessel wall caused by the bloodstream, mechanical action to the blood vessel wall caused by the pulsation of the heart (external force), the load condition of the blood vessel cross section boundary, the material model of the blood vessel wall, non-stress state of the blood vessel, geometric shape of the blood vessel wall, and the like. In this case, the mechanical action to the blood vessel wall caused by the bloodstream includes, for example, the internal pressure caused by the bloodstream and the shear stress caused by the bloodstream. Due to the internal pressure caused by the bloodstream, deformation occurs in the blood vessel circle or the direction perpendicular to the intravascular lumen surface. With the mechanical action to the blood vessel wall caused by the pulsation of the heart and the shear stress caused by the bloodstream, this generates deformation caused by the mechanical action applied to the blood vessel such as expansion and contraction, twisting, bending, and the like in the blood vessel center line direction. The deformation of the blood vessel such as expansion and contraction, twisting, bending, and the like in the blood vessel center line direction is allocated, as the load condition, to the aorta region R1, the right coronary artery region R2, and the left coronary artery region R3. More specifically, the deformation of the blood vessel such as expansion and contraction, twisting, bending, and the like in the blood vessel center line direction is expressed by a forced displacement (movement vector and rotation displacement) or a temporal change of a load vector. The deformation in the blood vessel circle or the direction perpendicular to the lumen surface based on the internal pressure caused by the bloodstream is allocated to the intravascular lumen as a temporal change of the pressure distribution.

The displacement constraint condition due to forced displacement is allocated to the aorta region R1, the right coronary artery region R2, and the left coronary artery region R3 in the structural fluid analysis. Therefore, the deformation freedom degree of the blood vessel wall in the structural fluid analysis can be reduced, and the calculation convergence can be stabilized, and the analysis time can be reduced.

For example, the deformation degree of the shape of the blood vessel depends on the material of the blood vessel wall. For this reason, the material model is allocated to the aorta region R1, the right coronary artery region R2, and the left coronary artery region R3. The deformation degree of the shape of the blood vessel also depends on the non-stress state of the blood vessel. The residual stress distribution of the blood vessel may be allocated as the initial value of the load condition.

The parameters about latent variables such as the material model, the boundary condition, and the load condition are identified by the inverse analysis (statistical identification processing) based on the dynamical model explained later. The accurate latent variables identified by the inverse analysis region allocated to the dynamical model. With the dynamical model to which accurate latent variables region allocated, the hemodynamics analysis can be executed based on structural fluid analysis or fluid analysis or structure analysis or image analysis in view of the effect to the analysis target blood vessel region due to the external factors such as the blood vessel and the heart outside of the analysis target blood vessel region. When the blood vessel analysis apparatus 50 structures the dynamical model, the blood vessel analysis apparatus 50 can solve the following four difficulties associated with a conventional example using the identification of the latent variables with the inverse analysis. Difficulty 1: identification method of the material model of the coronary artery. Difficulty 2: incorporation of the effect of deformation of the shape of the heart to the coronary artery. Difficulty 3: identification method of the boundary condition of the coronary artery. Difficulty 4: image analysis and structural fluid analysis using the blood vessel shape having variation based on uncertainty of medical image data. By overcoming the four difficulties, the blood vessel analysis apparatus 50 achieves the improvement of the analysis accuracy as compared with a conventional blood vessel structural fluid analysis in which latent variables are not identified with the inverse analysis.

Figure 3:
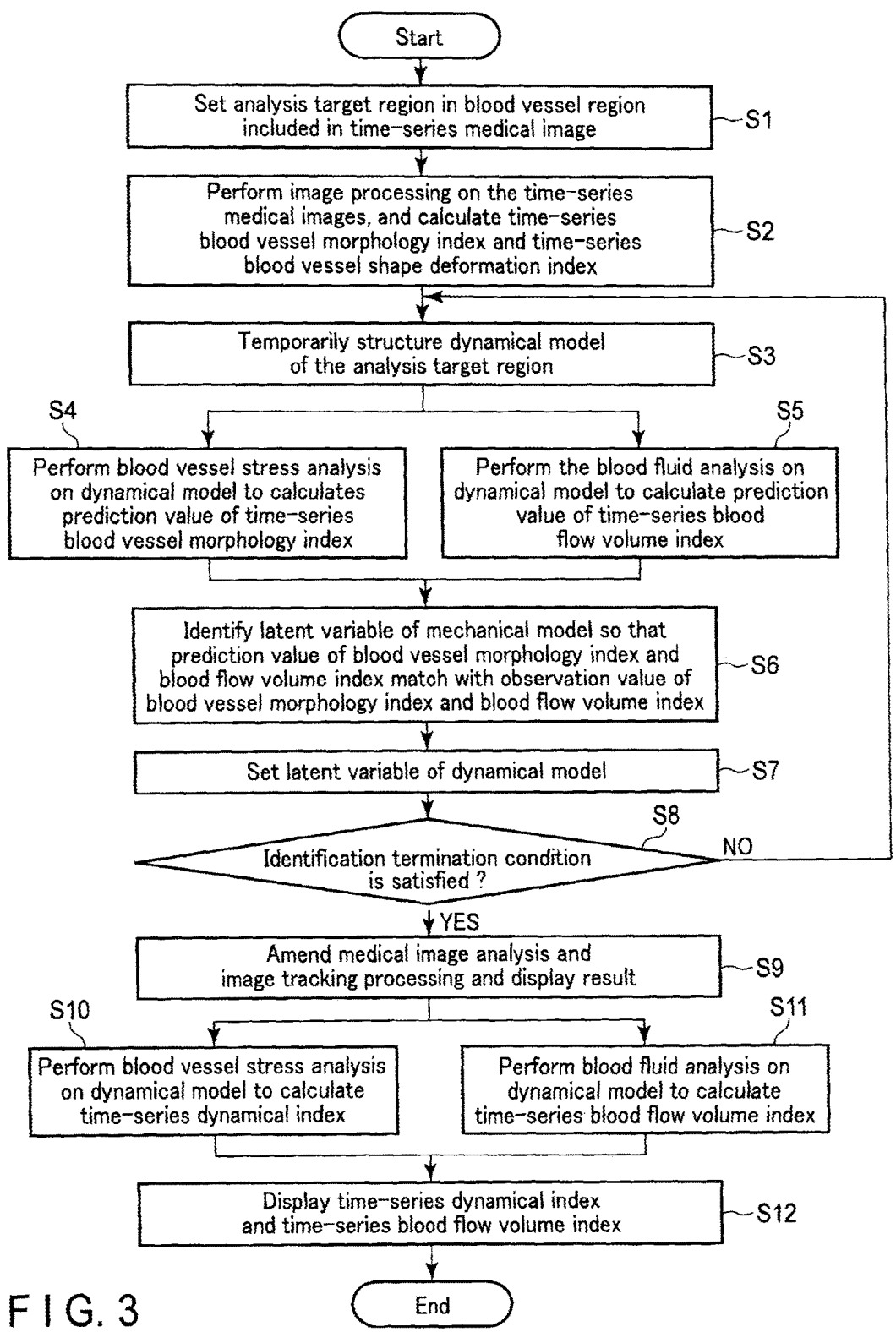
FIG. 3 is a figure illustrating a typical flow of structural fluid analysis processing performed under the control of a system control circuitry of FIG. 1.
Figure 4:
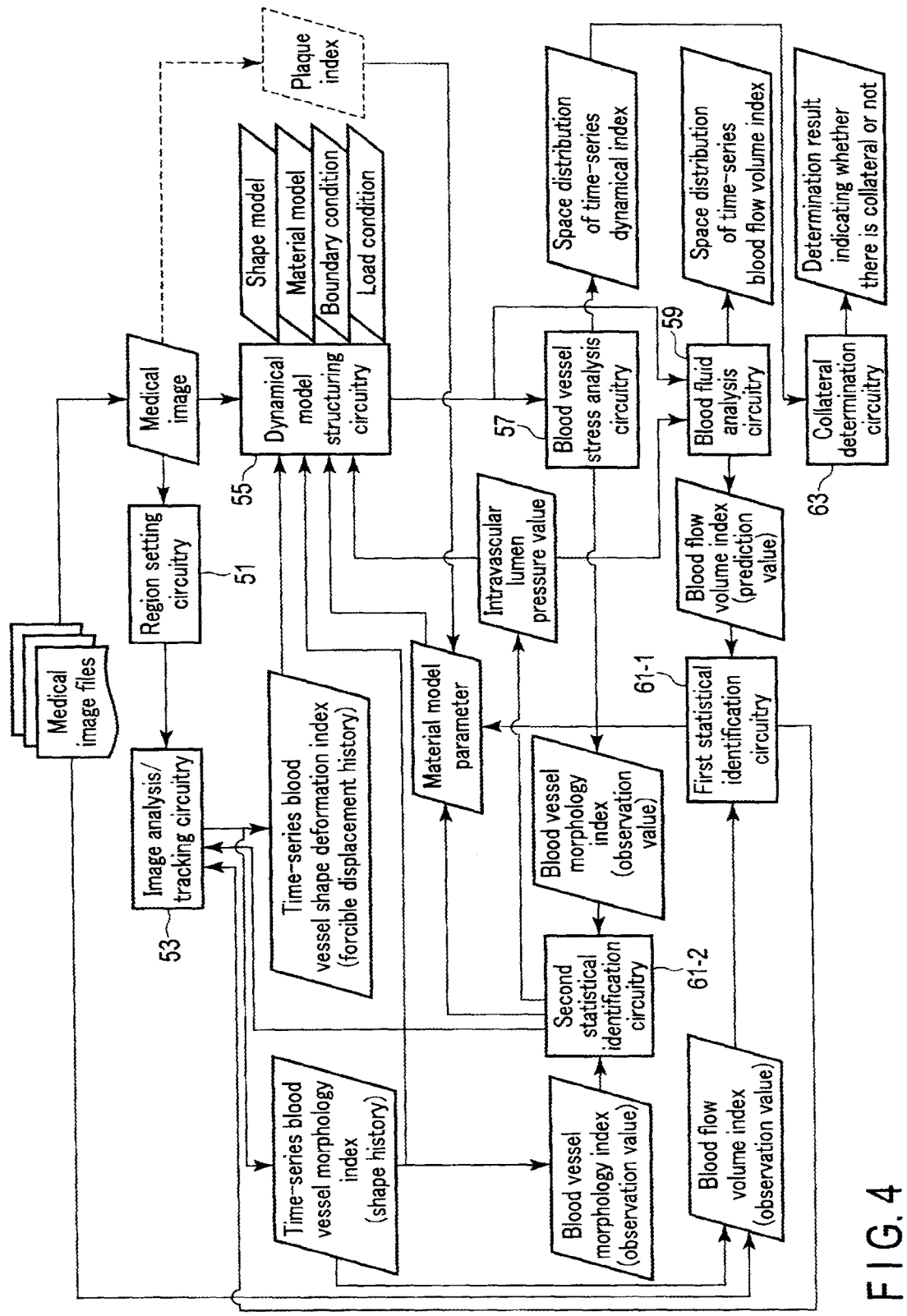
FIG. 4 is a figure illustrating a block configuration of the image processing circuitry of FIG. 1.

Subsequently, the details of the structural fluid analysis processing according to the present embodiment will be explained. FIG. 3 is a figure illustrating a typical flow of structural fluid analysis processing performed under the control of the system control circuitry 21 according to the present embodiment. FIG. 4 is a figure illustrating a block configuration of the image processing circuitry 27.

As shown in FIG. 3, in the structural fluid analysis processing, first, the system control circuitry 21 reads a medical image file of processing target from the storage 33, and provides the medical image file to the image processing circuitry 27. The medical image file includes not only data of time-series CT images but also data of observation value of the bloodstream index. The data of the time-series CT images are data representing three-dimensional space distribution of time-series CT values. The time-series CT images include, for example, 20 CT images per cardiac beat, and more specifically, the time-series CT images include, for example, CT images for about 20 cardiac phases.

As shown in FIG. 3, the system control circuitry 21 causes the image processing circuitry 27 to perform the region setting processing (step S1). In step S1, the region setting circuitry 51 of the image processing circuitry 27 sets the analysis target region of the structural fluid analysis in the blood vessel region included in the time-series CT image, and sets the identification target region of the latent variable in the analysis target region. The analysis target region may be all of the blood vessel region drawn in the time-series CT image, or may be a part thereof. For example, the analysis target region is set to any given part of the blood vessel region with regard to the coronary artery.

Figure 5:
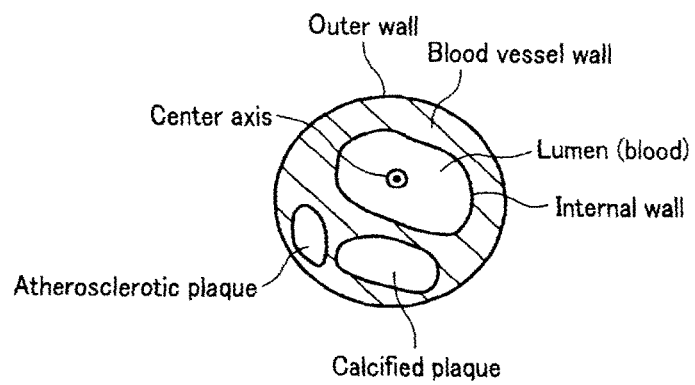
FIG. 5 is a figure schematically illustrating a cross section perpendicular to a center line of a blood vessel region included in a CT image.

In this case, a structure of a blood vessel drawn in a CT image will be explained with reference to FIG. 5. FIG. 5 is a figure schematically illustrating a cross section perpendicular to the center line of the blood vessel (hereinafter referred to as a center line longitudinal cross section). As shown in FIG. 5, the blood vessel includes a tube-like blood vessel wall. The pixel region corresponding to the blood vessel wall will be referred to as a blood vessel wall region. The center axis of the blood vessel wall will be referred to as an axial line. The inner side of the blood vessel wall will be referred to as an intravascular lumen. A pixel region corresponding to blood where blood and contrast agent flows in the lumen will be referred to as a blood region, and a pixel region corresponding to the contrast agent will be referred to as a contrast agent region. When the blood region and the contrast agent region are not particularly distinguished from each other, it will be referred to as a lumen region. The border between the lumen and the blood vessel wall is referred to as a blood vessel wall. Outside of the blood vessel wall, perivascular tissues such as cardiac muscles are distributed. The border between the blood vessel wall and the perivascular tissue is referred to as a blood vessel external wall. Inside of the blood vessel wall, a plaque may be generated. A pixel region corresponding to the plaque will be referred to as a plaque region. The plaque is classified into, for example, calcified plaque which has been calcified, atherosclerotic plaque, and the like. The atherosclerotic plaque is soft, and the blood vessel wall may break and exude to the inside of the blood vessel as a thrombus, and may be referred to as unstable plaque. Therefore, it is useful to find the property of the plaque in a clinical manner. As explained later, the property and the existing region of the plaque may be identified by a CT value.

For example, the analysis target region is set by the region setting circuitry 51 to be limited into a lesion region or a treatment target according to a command given with the input device 29 by the user. For example, in a case where a lesion region such as a plaque and a stenosed portion is found by image diagnosis and the like in advance, the pathologic change portion may be set as the analysis target region. Alternatively, the analysis target region may be limited in accordance with a clinical empirical rule associated with a lesion region. For example, a pathologic change generated in the heart blood vessel is likely to be generated in the blood vessel running on the surface of the heart. In general, the blood vessel running on the surface of the heart is thicker than the blood vessel entering into the inside of the heart. Therefore, the region setting circuitry 51 may set the analysis target region in the blood vessel region associated with the blood vessel running on the surface of the heart according to the image processing or the command given with the input device 29 by the user. For example, the region setting circuitry 51 may set the analysis target region to be limited into a blood vessel region where the diameter is equal to or more than 2 mm. In other words, the region setting circuitry 51 excludes the blood vessel region associated with the blood vessel in the inside of the heart from the analysis target region. As described above, the processing efficiency can be improved by decimating the calculation target in a spatial manner.

When step S1 is performed, the system control circuitry 21 causes the image processing circuitry 27 to perform image analysis/tracking processing (step S2). In step S2, the image analysis/tracking processing unit 53 of the image processing circuitry 27 performs image processing on the time-series CT images, and calculates time-series blood vessel morphology index and the time-series blood vessel shape deformation index. More specifically, the image analysis/tracking processing unit 53 performs the image analysis processing on the time-series CT image to calculate the time-series blood vessel morphology index, and performs tracking processing on the time-series CT image to calculate the time-series blood vessel shape deformation index. The blood vessel morphology index is an index representing a mode of a blood vessel region. A specific example of a blood vessel morphology index will be explained later.

Hereinafter, image analysis/tracking processing will be explained in a specific manner. In the image analysis processing, the image analysis/tracking processing unit 53 extracts the blood vessel region from each CT image, and identifies an intravascular lumen region, a blood vessel wall region, and a plaque region as shown in FIG. 5. The image analysis/tracking processing unit 53 identifies, as blood vessel morphology indexes, three-dimensional coordinates of multiple pixels included in contours of the intravascular lumen region, the blood vessel wall region, and the plaque region. A three-dimensional coordinate of a pixel is used as a blood vessel morphology index. It should be noted that pixels of a particular target of a three-dimensional coordinate may be limited to pixels included in the contours of the intravascular lumen region, the blood vessel wall region, and the plaque region in a surface perpendicular to the intravascular lumen surface or the blood vessel center line longitudinal cross section. It should be noted that the blood vessel morphology index may be not only the three-dimensional coordinate but also geometric indexes such as a direction vector of zero degrees and a radius and a diameter of the intravascular lumen for every angle in the blood vessel center line longitudinal cross section, an average region size and an average radius for all the angles in the cross section, an intravascular lumen capacity enclosed by multiple cross sections perpendicular to the center line direction, a blood vessel wall capacity and a plaque capacity enclosed by multiple cross sections perpendicular to the lumen surface.

In the tracking processing, the image analysis/tracking processing unit 53 sets multiple feature points such as feature points, feature shapes, representative points, and pixels, in the blood vessel wall region and the contrast agent region, according to the image processing or the command given with the input device 29 by the user. For example, the image analysis/tracking processing unit 53 sets multiple feature points such as a blood vessel branching portion and an anatomical feature point on a surface. The image analysis/tracking processing unit 53 applies image tracking processing to multiple feature points at each time (each cardiac phase), and calculates displacement values of multiple feature points. The image analysis/tracking processing unit 53 calculates a temporal change of a displacement value for each of multiple nodes in the dynamical model based on the calculated displacement value by the interpolation processing. For example, the image analysis/tracking processing unit 53 defines the node on the blood vessel center line in the dynamical model. The image analysis/tracking processing unit 53 may calculate the time-series deformation values (time change of the deformation value) of twisting, bending, and expansion and contraction in the center line direction of the blood vessel based on the time-series displacement value of nodes in the dynamical model (time change of the displacement value). As explained later, the blood vessel shape deformation indexes such as the displacement value and the deformation value are used as forced displacement in the dynamical model. Hereinafter the time-series blood vessel morphology index will be referred to as a shape history, and the time-series blood vessel shape deformation index will be referred to as a forced displacement history.

Figure 6:
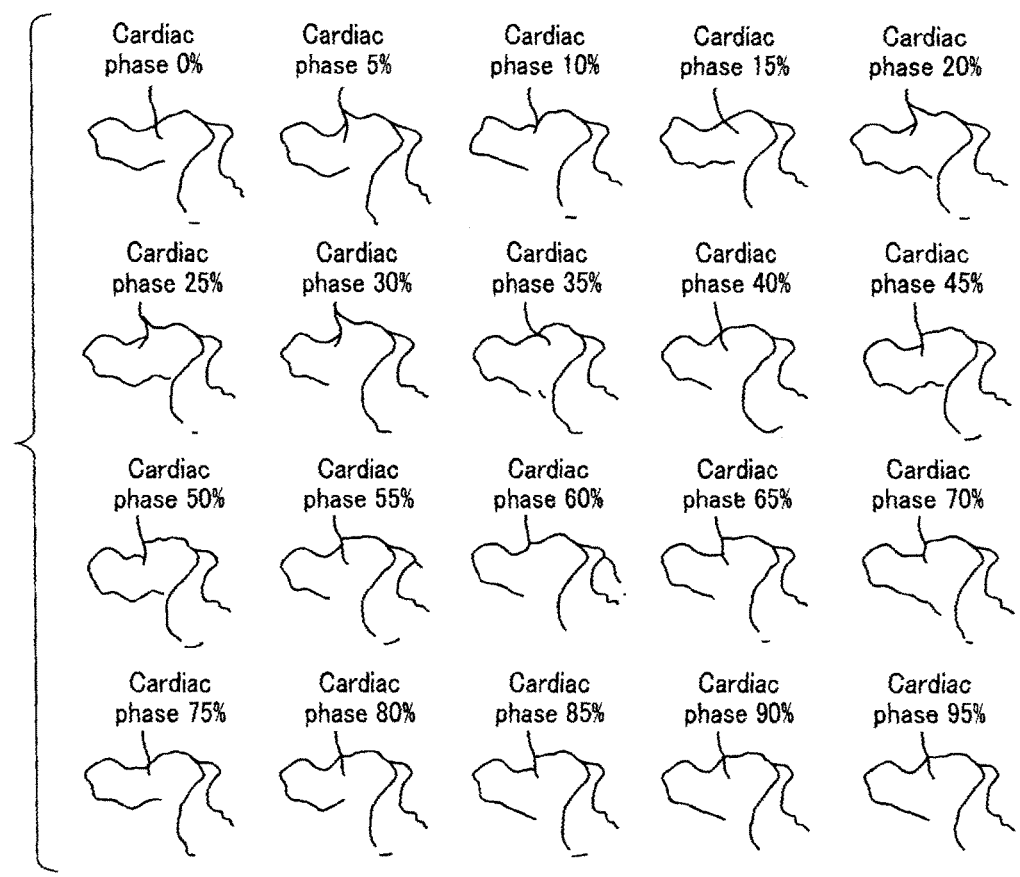
FIG. 6 is a figure illustrating a time change of an aspect of a blood vessel center line used for image tracking processing performed with image analysis/tracking processing of FIG. 4.

FIG. 6 is a figure illustrating a temporal change of a mode of a center line of a blood vessel region included in a CT image. As shown in FIG. 6, for example, the time-series medical images include 20 CT images per cardiac beat. More specifically, CT images are considered to be obtained with an interval of 5% from the cardiac phases 0% to 95%. The center line of the blood vessel region is extracted by the image analysis/tracking processing unit 53. As shown in FIG. 6, the mode of the center line changes in accordance with the elapse of the cardiac phase.

Figure 7:
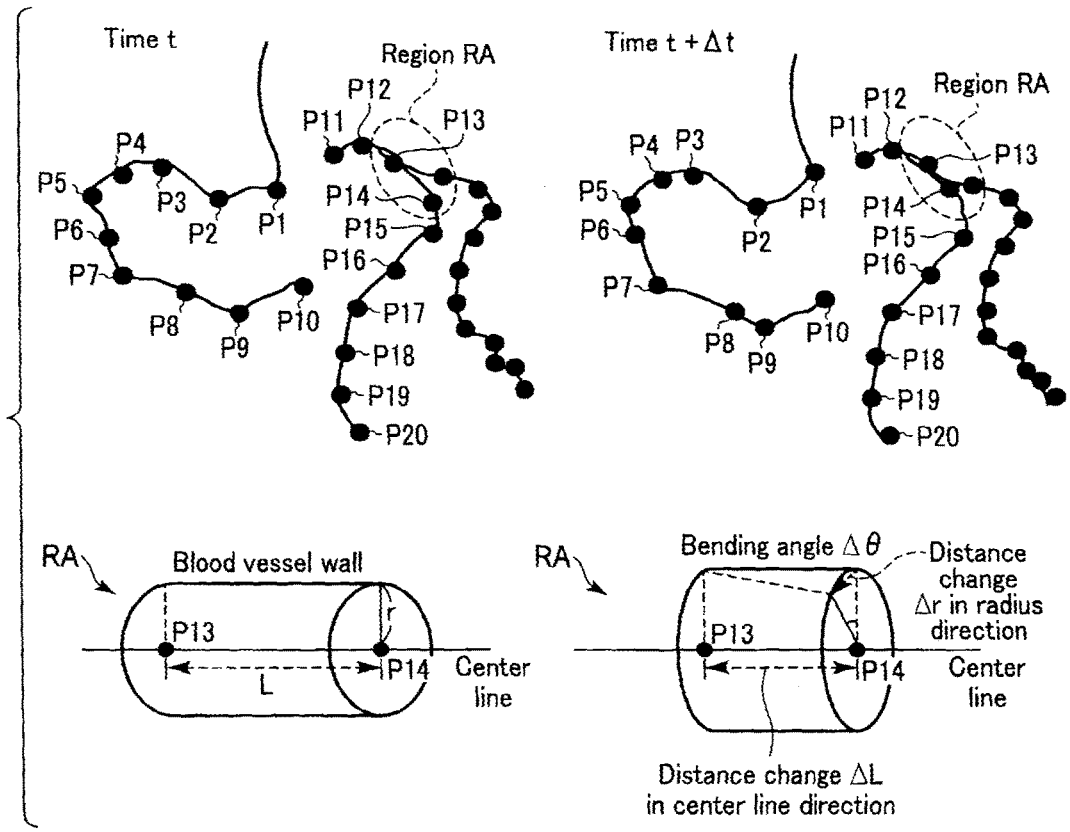
FIG. 7 is a figure for explaining image tracking processing according to the image analysis/tracking processing of FIG. 4, and is a figure illustrating an example of tracking processing between a time t and a time t+Δt.

FIG. 7 is a figure illustrating an example of tracking processing between a time t and a time t+Δt. As shown in FIG. 7, the nodes of the dynamical model from P1 to P20 are set on the blood vessel center lines. Each of the nodes of the dynamical model from P1 to P20 on the blood vessel center line is mechanically connected to other nodes of the dynamical model on the center line longitudinal cross section including the node. However, they are independent from the nodes of the dynamical model of the blood. Based on the displacement values of the feature points of the blood vessel, the displacement values of the nodes of P1 to P20 on the blood vessel center line are calculated by processing such as interpolation, and the forced displacement is set for each node.

In order to explain the blood vessel shape deformation index and the blood vessel morphology index, a local blood vessel region RA defined by the node P13 and the node P14 will be considered. At a time t, the distance between the node P13 and the node P14 in the center line direction is considered to be L, and the radius in the blood vessel region is considered to be r. The image analysis/tracking processing unit 53 calculates forced displacement such as expansion and contraction, twisting, and bending in the blood vessel center line direction of the node P13 and the node P14, so that the forced displacement at the node P13 (the movement displacement in the three-dimensional space and the rotation displacement in the center line direction) and the forced displacement at the node P14 (the movement displacement in the three-dimensional space and the rotation displacement in the center line direction) are calculated.

As shown in FIGS. 6 and 7, the image analysis/tracking processing unit 53 calculates the forced displacement at each node on the center line (the movement displacement in the three-dimensional space and the rotation displacement rotating about the center line) based on the coordinate and the movement vector of the feature point, and calculates the blood vessel shape deformation index. For example, the image analysis/tracking processing unit 53 calculates a time change of a coordinate difference of two adjacent nodes is calculated as the expansion and contraction distance $\Delta L$ in the center line. With regard to each node on the center line, the image analysis/tracking processing unit 53 calculates a time change of a distance between the node in question and another node on the blood vessel region cross section including the node in question (the node in the intravascular lumen or the blood vessel wall or the plaque region) as the expansion and contraction distance $\Delta r$ in the radius direction. With regard to each feature point, the image analysis/tracking processing unit 53 calculates a bending angle $\Delta \theta$ in the center line direction of the node in question on the center line based on the coordinates and the movement vectors of multiple feature points in proximity to the feature point.

In the above example, the spatial resolution of the time-series CT image of the analysis target is expected to be constant over the elapse of the time. However, the analysis target according to the present embodiment is not limited thereto.

For example, the X-ray computed tomography apparatus according to the present embodiment may generate time-series CT images by executing CT scan so that the temporal resolution of a designation section is higher than the temporal resolution of another section. It should be noted that setting the temporal resolution of a designation section to be higher than the temporal resolution of another section is considered to include a case where the temporal resolution of the another section is set to be lower than the temporal resolution of the designation section. A CT image outside of the designation section where the temporal resolution is reduced may be interpolated based on another CT image adjacent to the CT image in question in terms of time. For example, the designation section is set to a designation section in which the temporal resolution is to be set to be higher and which is designated with the input device 29 by the user. For example, the designation section may be designated in a time section where movement of the blood vessel is intense. In a typical case, the movement of the blood vessel is relatively slow during expansion and contraction, and the noise of the time-series CT image is relatively low. Therefore, the designation section is preferably set between the expansion and the contraction. Alternatively, a time section where the motion is relatively slow such as expansion and contraction may be set as the designation section. A CT image in this time section when the motion is intense is preferably interpolated based on a CT image in another time. Therefore, this can reduce noises in the CT images in the time section where the motion of the blood vessel and the like is intense, and further, enhance the accuracy of the structural fluid analysis. As described above, the calculation time associated with the structural fluid analysis can be reduced by decimating the CT images in terms of time.

The method for decimating the CT images of the analysis target in terms of time is not limited to changing the temporal resolution of the CT scan along the elapse of the time. For example, a CT image used for the structural fluid analysis may be individually selected from original time-series CT images reconfigured by the reconstruction circuitry 25. For example, the above designation section is preferably set in the original time-series CT image. In this case, a CT image is preferably selected in a denser manner in terms of time in the designation section than in other sections.

When step S2 is performed, the system control circuitry 21 causes the image processing circuitry 27 to perform the structuring processing (step S3). In step S3, the dynamical model structuring circuitry 55 of the image processing circuitry 27 temporarily structures the dynamical model about the analysis target region based on the time-series CT image. More specifically, the dynamical model structuring circuitry 55 temporarily structures the dynamical model about the analysis target region based on the time-series CT image and the forced displacement history and the shape history calculated based on the time-series CT image. The dynamical model is a numerical model about the analysis target region for performing the structural fluid analysis.

Hereinafter, step S3 will be explained in details. First, the dynamical model structuring circuitry 55 structures the shape model for solving the dynamical model (mathematical model) based on the CT image and the shape history. The shape model schematically expresses the geometric structure of the blood vessel region at each cardiac phase. The shape model is classified into, for example, multiple discretized regions. The vertex of each of the discretized regions is referred to as a node. The dynamical model structuring circuitry 55 may structure the shape model for each cardiac phase based on the blood vessel region and the blood vessel morphology index included in the CT image for each cardiac phase, and may structure the shape model for each cardiac phase based on the blood vessel region and the blood vessel morphology index included in the CT image of a particular cardiac phase. For example, when it is assumed that there is no residual stress in the blood vessel corresponding to the analysis target region in the initial load state, a time phase at which the blood vessel corresponding to the analysis target region is most greatly contracted in the time phase of the non-stress state is assumed to be a non-stress state.

Figure 8:
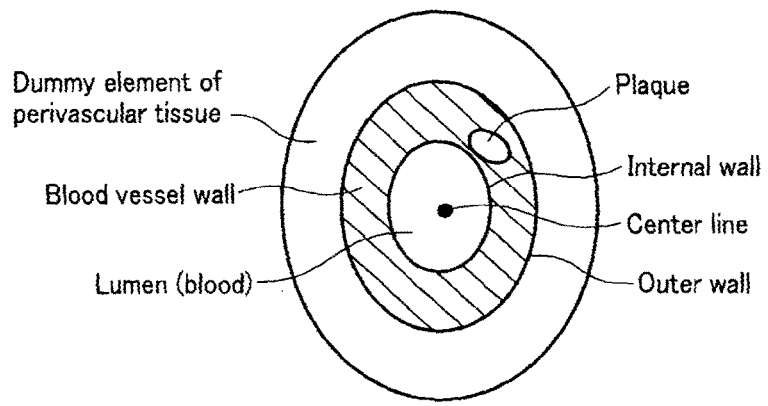
FIG. 8 is a figure illustrating a cross section perpendicular to a center line of a shape model structured by a dynamical model structuring circuitry of FIG. 4.

FIG. 8 is a figure illustrating a cross section perpendicular to a center line of a shape model. As shown in FIG. 8, the shape model has an intravascular lumen region and a blood vessel wall region which region arranged from the center line to the outside. When there is a plaque, a plaque region may be provided in the blood vessel wall region. When the effect to the blood vessel by the perivascular tissue is taken into consideration, the dummy element of the perivascular tissue may be provided outside of the blood vessel wall region.

When the shape model is structured, the dynamical model structuring circuitry 55 sets the sampling value about the parameter of the latent variable obtained from the variable range and the probability distribution of each latent variable (for example, sampling from a set of combination of parameters based on Markov chain Monte Carlo method and the like) to the dynamical model. For example, as shown in FIG. 2, the dynamical model structuring circuitry 55 sets the region of the identification target of the boundary condition about the entrance (hereinafter referred to as a boundary condition identification region) at the end of the aorta region R1 at the side of the origin of the aorta, and sets the boundary condition identification region about the exit at the end of the right coronary artery region R2 and the end of the left coronary artery region R3. The dynamical model structuring circuitry 55 allocates the sampling value about the parameter of the boundary condition obtained from the variable range and the probability distribution of the boundary condition to each boundary condition identification region. The dynamical model structuring circuitry 55 also sets the region of the identification target of the material model (hereinafter referred to as a material model identification region) and the region of the identification target of the load condition (hereinafter referred to as a load condition identification region) in the aorta region R1, the right coronary artery region R2, and the left coronary artery region R3. The dynamical model structuring circuitry 55 allocates the sampling value about the parameter of the material model obtained from the variable range and the probability distribution of the material model to each material model identification region, and allocates the sampling value about the parameter of the load condition obtained from the variable range and the probability distribution of the load condition to each load condition identification region. In the blood vessel, even when the volume of flow is zero, it is said that there is a residual stress. For example, the dynamical model structuring circuitry 55 may allocate the residual stress in a case where the volume of flow is zero to the analysis target region as the initial value of the load condition. The dynamical model structuring circuitry 55 may set an region of identification target of the geometric structure (hereinafter referred to as a geometric structure identification region) to a portion where there is uncertainty in the geometric structure. It should be noted that the parameter of the geometric structure is a variation distribution parameter related to uncertainty of the geometric structure, or a variation distribution parameter involved in the CT image, and may be, e.g., a variation distribution of the boundary threshold value of the living tissue and the variation distribution of each CT value. The dynamical model structuring circuitry 55 may set the material model in the plaque region, the details of which will be explained later. The details of the material model will be explained later.

The initial value of the boundary condition according to the fluid analysis may be calculated based on the time-series CT image. In the CT scan using the contrast agent, the X-ray computed tomography apparatus repeatedly performs scan with a lose dose on a scan region while injecting the contrast agent into the subject, and monitors the contrast agent density of the blood vessel in the scan region. Then, the X-ray computed tomography apparatus performs scan with a normal dose when the contrast agent density attains the already-determined value. The scan for monitoring of the contrast agent density is referred to as a pre-scan. The dynamical model structuring circuitry 55 may calculate the initial value of the boundary condition according to the fluid analysis based on the time-series CT image collected by pre-scan (so-called prep image). For example, the dynamical model structuring circuitry 55 sets an region of interest (ROI) in the time-series CT image according to the command given with the input device 29 by the user. The ROI is preferably set in the boundary condition identification region such as an entrance of the analysis target blood vessel. The dynamical model structuring circuitry 55 calculates parameters such as an initial speed and a flow-in volume of bloodstream in the ROI based on time change of a pixel region of the contrast agent included in the ROI (hereinafter referred to as a contrast agent region). For example, the dynamical model structuring circuitry 55 applies image tracking processing to the contrast agent region, thus calculating the parameters such as the initial speed and the flow-in volume of the bloodstream. The convergence time of the parameter of the latent variable can be reduced by calculating the initial value of the boundary condition based on the time-series CT image.

In order to easily identify the material model parameter, the dynamical model structuring circuitry 55 may determine the material model parameter allocated to the material model identification region based on the CT value of a pixel in the material model identification region. As described above, the CT value is used as a plaque index for estimating the property of the plaque. Hereinafter, the determination processing of the material model parameter based on the CT value will be explained using an example of blood vessel wall.

The CT value is an index making the degree of attenuation of the X-ray into a number in a relative manner. Therefore, the CT value has a different value for a different living tissue, and in other words, the CT value is scaled as necessary so that the difference of the tissue can be recognized. The storage 33 includes a table storing each of the properties of multiple blood vessel walls in association with the CT value range and the material model parameter. Hereinafter, this table will be referred to as a CT value— material model table.

Figures 9, 10:
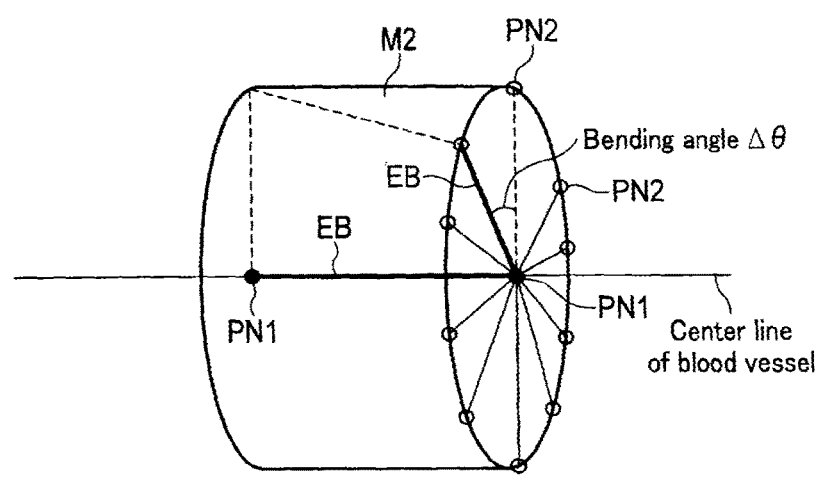
FIG. 9 is a figure illustrating an example of a CT value—material model table stored in a storage of FIG. 1.
FIG. 10 is a figure for explaining allocation of a forced displacement history to a shape model performed by the dynamical model structuring circuitry of FIG. 4.

FIG. 9 is a figure illustrating an example of a CT value—material model table stored in the storage 33. As shown in FIG. 9, the CT value—material model table includes items, i.e., the property of the blood vessel wall, a CT value range, and a material model parameter. Examples of properties include normal, atherosclerotic plaque, and calcified plaque. For each property, the empirically defined CT value range and the material model parameter region associated with each other. The material model parameter may be defined by any given numeral, or may be defined in a numerical range. First, the dynamical model structuring circuitry 55 determines the representing pixel value in the ROI included in the CT image. The ROI is set in the identification target region of the material model according to the image processing or the command given with the input device 29 by the user. For example, the representing pixel value is set to a statistical value such as an average value, a median value, a modal value, a maximum value, and a minimum value of pixel values of multiple pixels included in the ROI. The dynamical model structuring circuitry 55 identifies the material model parameter associated with the representing pixel value by applying the determined representing pixel value to the CT value—material model table. The dynamical model structuring circuitry 55 allocates the identified material model parameter to the material model identification region on the dynamical model corresponding to the ROI. As described above, by initially designating the material model parameter based on the CT value, the search range of the parameter in the inverse analysis performed later can be stenosed. Therefore, reduction of the calculation time can be realized.

When the shape model is structured, the dynamical model structuring circuitry 55 allocates the time-series blood vessel shape deformation index calculated in step S2 to the shape model, and more specifically, the dynamical model structuring circuitry 55 allocates the forced displacement history to the shape model. The shape model to which the latent variable and the forced displacement history region allocated will be referred to as a dynamical model.

In FIG. 10, the shape model M2 illustrates a portion of the dynamical model of the blood vessel and the blood, and FIG. 10 is a figure for explaining allocation of the forced displacement history to the node in the dynamical model. FIG. 10 illustrates a portion of the shape model M2. However, although FIG. 10 shows a case where the center line is located in the M2, the center line may also be located outside of the M2. As shown in FIG. 10, multiple nodes PN (PN1, PN2) are set in the shape model M2. The node on the center line is referred to as PN1, and the nodes in the dynamical model indicating the blood vessel and the blood will be referred to as PN2. The shape model M2 is set for the dummy element surface, blood vessel external wall, blood vessel wall, plaque region surface, plaque region internal, or blood portion. The dynamical model structuring circuitry 55 allocates the forced displacement to each node PN1 of the shape model M2, and more specifically, allocates the blood vessel shape change index for each time.

More specifically, the dynamical model structuring circuitry 55 connects the node PN1 and the node PN1, which region adjacent to each other on the center line, with a beam element (or rigid element) EB. The dynamical model structuring circuitry 55 connects the node PN1 and another node PN2 included in a longitudinal cross section passing through the node PN1 with a beam element EB. The dynamical model structuring circuitry 55 allocates the constraint condition about the shape displacement direction of each blood vessel shape deformation index to the node PN1 and the beam element EB. The forced displacement allocated to the region where the internal pressure of the material model and the intravascular lumen is identified includes the expansion and contraction of the blood vessel wall (or dummy element) surface in the center line direction, the twisting of the blood vessel wall (or dummy element) surface, and the bending deformation of the blood vessel wall (or dummy element) surface. For example, the forced displacement allocated to the region where the internal pressure of the material model and the intravascular lumen is not identified includes not only the forced displacement in the center line direction and the time-series expansion and contraction (displacement) of the blood vessel wall in the radius direction. In a case where the internal pressure affects deformation outside of the center line longitudinal cross section, the forced displacement is not allocated to the region, and the forced displacement history is allocated to only the peripheral portion of the region (for example, the surface node of the dummy element). Cases where the internal pressure contributes to deformation outside of the center line longitudinal cross section includes a case where there is a protrusion on the intravascular lumen and the blood vessel branching portion and the like. The dynamical model structuring circuitry 55 allocates the time-series blood vessel shape deformation index to the node PN1 and the beam element EB as the forced displacement history. In this manner, the expansion and contraction deformation, the twisting deformation, and the bending deformation about the entire blood vessel or the local portion thereof are expressed.

In FIG. 10, the forced displacement history is set for the center line unit and the external wall unit of the shape model, but the setting portion of the forced displacement history is not limited thereto. For example, the forced displacement history may be set in the blood vessel wall region between the center line unit and the external wall unit.

The image processing circuitry 27 according to the present embodiment performs inverse analysis using the mechanical model temporarily structured in step S3, and statistically identifies the latent variable that is set in the dynamical model. The statistical identification processing is performed in step S6 explained later. Steps S4 and S5 are provided to calculate the blood vessel morphology index and the bloodstream index used for the statistical identification processing.

When step 3 is performed, the system control circuitry 21 causes the image processing circuitry 27 to perform the blood vessel stress analysis processing (step S4). In step S4, the blood vessel stress analysis circuitry 57 of the image processing circuitry 27 performs the blood vessel stress analysis on the dynamical model of the current stage, and calculates prediction value of the time-series blood vessel morphology index. The blood vessel morphology index may be any of blood vessel morphology indexes explained above, and, for example, it is preferable to use the cross section shape index of the lumen region in the blood vessel center line direction and the cross section shape index of the blood vessel wall. More specifically, the cross section shape index of the lumen region is any one of the coordinate value of the attention-given pixel in the lumen region and the geometric structure parameter in the lumen region (the radius of the lumen region, the diameter of the lumen region, and the like). More specifically, the cross section shape index in the blood vessel wall region is any one of the coordinate value of the attention-given pixel in the blood vessel wall region and the geometric structure parameter in the blood vessel wall region (the radius of the blood vessel wall region, the diameter of the wall region, and the like). It should be noted that the prediction value means the calculation value of the blood vessel morphology index calculated by performing the blood vessel stress analysis on the dynamical model.

When step 3 is performed, the system control circuitry 21 causes the image processing circuitry 27 to perform the blood fluid analysis processing (step S5). In step S5, the blood fluid analysis circuitry 59 of the image processing circuitry 27 performs the blood fluid analysis to the temporarily structured dynamical model to calculate the prediction value of the time-series blood flow volume index. The blood flow volume index is the volume of blood flow or the flow rate. The bloodstream index may be any one of the volume of blood flow or flow rate, and a spatial or temporal average value of the volume of blood flow or flow rate. It should be noted that the prediction value means the calculation value of the blood fluid index calculated by performing the blood fluid analysis on the dynamical model.

When steps S4 and S5 are performed, the system control circuitry 21 causes the image processing circuitry 27 to perform the identification processing (step S6). In step S6, the statistical identification circuitry 61 of the image processing circuitry 27 statistically identifies the parameter of the latent variable of the mechanical model so that at least one of the prediction value of the blood vessel morphology index calculated in step S4 and the prediction value of the bloodstream index calculated in step S5 are in conformity with at least one of the observation value of the blood vessel morphology index and the observation value of the bloodstream index collected in advance.

As shown in FIG. 4, the statistical identification circuitry 61 includes a first statistical identification circuitry 61-1 and a second statistical identification circuitry 61-2. The first statistical identification circuitry 61-1 statistically identifies the parameter of the latent variable so that the prediction value of the blood vessel morphology index is in conformity with the observation value of the blood vessel morphology index. The second statistical identification circuitry 61-2 statistically identifies the parameter of the latent variable so that the prediction value of the bloodstream index is in conformity with the observation value of the bloodstream index. Hereinafter, the first statistical identification circuitry 61-1 and the second statistical identification circuitry 61-2 will be explained in order.

More specifically, in step S6, the first statistical identification circuitry 61-1 sets the data distribution based on the prediction value and the observation value of the blood vessel morphology index calculated in step S4. The data distribution indicates, for example, a multivariate normal distribution function about an error of the prediction value and the observation value of the blood vessel morphology index. More specifically, the first statistical identification circuitry 61-1 calculates the normal distribution function value of the error between the prediction value and the observation value for each node or each element in the dynamical model. The first statistical identification circuitry 61-1 sets a product of each calculated normal distribution function value as data distribution. The data distribution may be set individually for each cardiac phase, or may be set collectively for multiple cardiac phases.

Subsequently, the first statistical identification circuitry 61-1 allocates prior distribution (prior probability distribution) to the latent variable of the dynamical model. More specifically, the prior distribution is allocated to each parameter related to material model, boundary condition, load condition, and uncertainty of the shape deformation index and the time-series morphology index. For example, the prior distribution related to the pressure value is allocated to the pressure value related to the intravascular lumen which is one of the parameters of the load condition. The range of the value that can be taken by the pressure value (hereinafter referred to as expected range) can be limited empirically in advance. The first statistical identification circuitry 61-1 executes Monte Carlo simulation of the internal pressure value with limitation within the expected range, so that the probability distribution of the internal pressure value, i.e., the prior distribution, is calculated for each discretized region. For example, the first statistical identification circuitry 61-1 may set, as the prior distribution, a probability distribution mathematically expressed by a multivariate normal distribution function indicating that the inclination of average pressure change in the center line direction is negative in a predetermined case. Examples of predetermined cases include a case where the pressure distribution in the center line direction is smooth, a case where the pressure change over the elapse of the time is smooth, and a case where any backward flow of bloodstream is observed. In accordance with the probability distribution expected by being limited into the expected range, first statistical identification circuitry 61-1 executes the Monte Carlo simulation about the parameter of the load condition, and can obtain the sampling value of the load condition for setting in the dynamical model (latent variable). Subsequently, the first statistical identification circuitry 61-1 performs the statistical identification processing on the prior distribution and the data distribution for each latent variable, and calculates the posterior distribution (posterior probability distribution). The statistical identification processing includes, for example, hierarchical Bayesian model and Markov chain model. Then, the first statistical identification circuitry 61-1 identifies the parameter of each latent variable from the statistical value such as the modal value and the average value of the posterior distribution for each latent variable. For example, in the above example, the posterior distribution of the intravascular lumen pressure value is calculated, and the identification value of the intravascular lumen pressure value is calculated from the posterior distribution.

Figure 11:
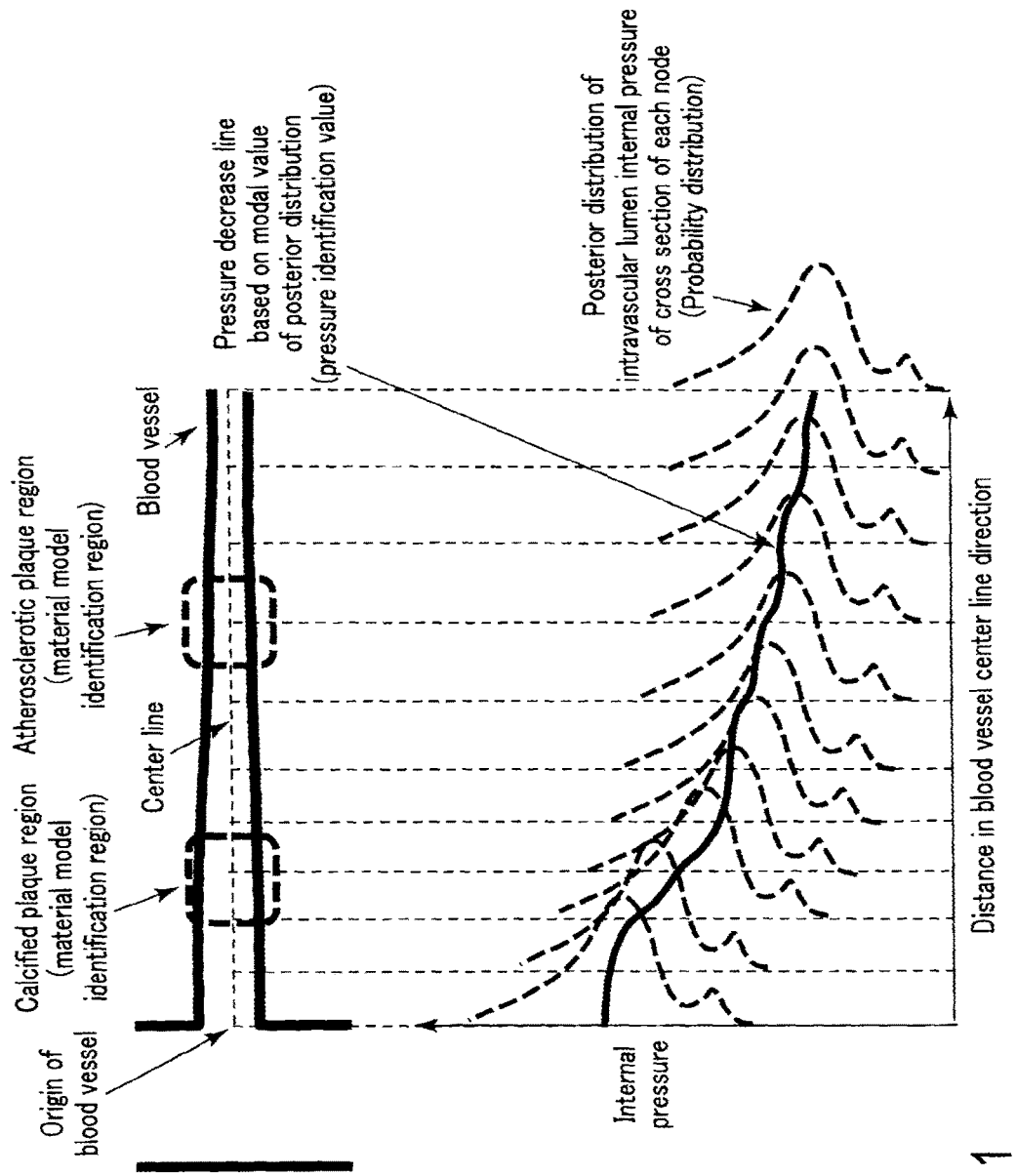
FIG. 11 is a figure for explaining posterior distribution calculation and identification of an average internal pressure of a load condition (an average pressure in a blood vessel) according to hierarchical Bayesian model and Markov chain Monte Carlo methods performed by the statistical identification circuitry of FIG. 4.

FIG. 11 is a figure for explaining identification of the average internal pressure and the posterior distribution calculation about the load condition based on hierarchical Bayesian model and Markov chain Monte Carlo method (the average pressure in the blood vessel). In the graph as shown in FIG. 11, the vertical axis is defined as the internal pressure value, and the horizontal axis is defined as the distance from the blood vessel origin in the blood vessel center line direction. As shown in FIG. 11, The calcified plaque region is set in the material model identification region, and in the atherosclerotic plaque region, the material model identification region is set. The blood vessel internal pressure decreases along the blood vessel center line direction from the blood vessel origin. Multiple nodes are set along the blood vessel center line. In the longitudinal cross section (node cross section) including each node, the posterior distribution of the lumen internal pressure is calculated, and the modal value of the posterior distribution is identified.

For example, the blood vessel morphology index calculated in step S2 is used as the observation value of the blood vessel morphology index.

The processing performed by the second statistical identification circuitry 61-2 is the same as the processing performed by the first statistical identification circuitry 61-1 only in that the index used for calculation of the data distribution is different. More specifically, first, the second statistical identification circuitry 61-2 sets the data distribution based on the prediction value and the observation value of the bloodstream index calculated in step S5. Subsequently, the second statistical identification circuitry 61-2 allocates the prior distribution to the latent variable of the dynamical model. For example, the prior distribution of the parameter of the material model about the blood vessel, the parameter of the material model about the blood, and the parameter of the material model about the plaque region allocated. Examples of parameters of the material model include material model parameters such as parameters of an elastic modulus and viscosity of the constitutive equation of the blood. The probability distribution and the expected range of the parameter of the material model can be set empirically in advance. The second statistical identification circuitry 61-2 sets the probability distribution of the parameter of the material model for each discretized region, and more specifically, the second statistical identification circuitry 61-2 sets the prior distribution, and in accordance with the expected probability distribution limited into the expected range, the Monte Carlo simulation of the parameter of the material model can be executed, and the sampling value of the material model parameter for setting in the dynamical model (latent variable) can be obtained. Subsequently, the second statistical identification circuitry 61-2 calculates the posterior distribution by performing the statistical identification processing on the prior distribution and the data distribution for each latent variable, and identifies the parameter of each latent variable from the statistical value of the calculated posterior distribution. For example, in the above example, the posterior distribution of the parameter of the material model is calculated, and the identification value of the parameter of the material model is calculated from the posterior distribution.

Figure 12:
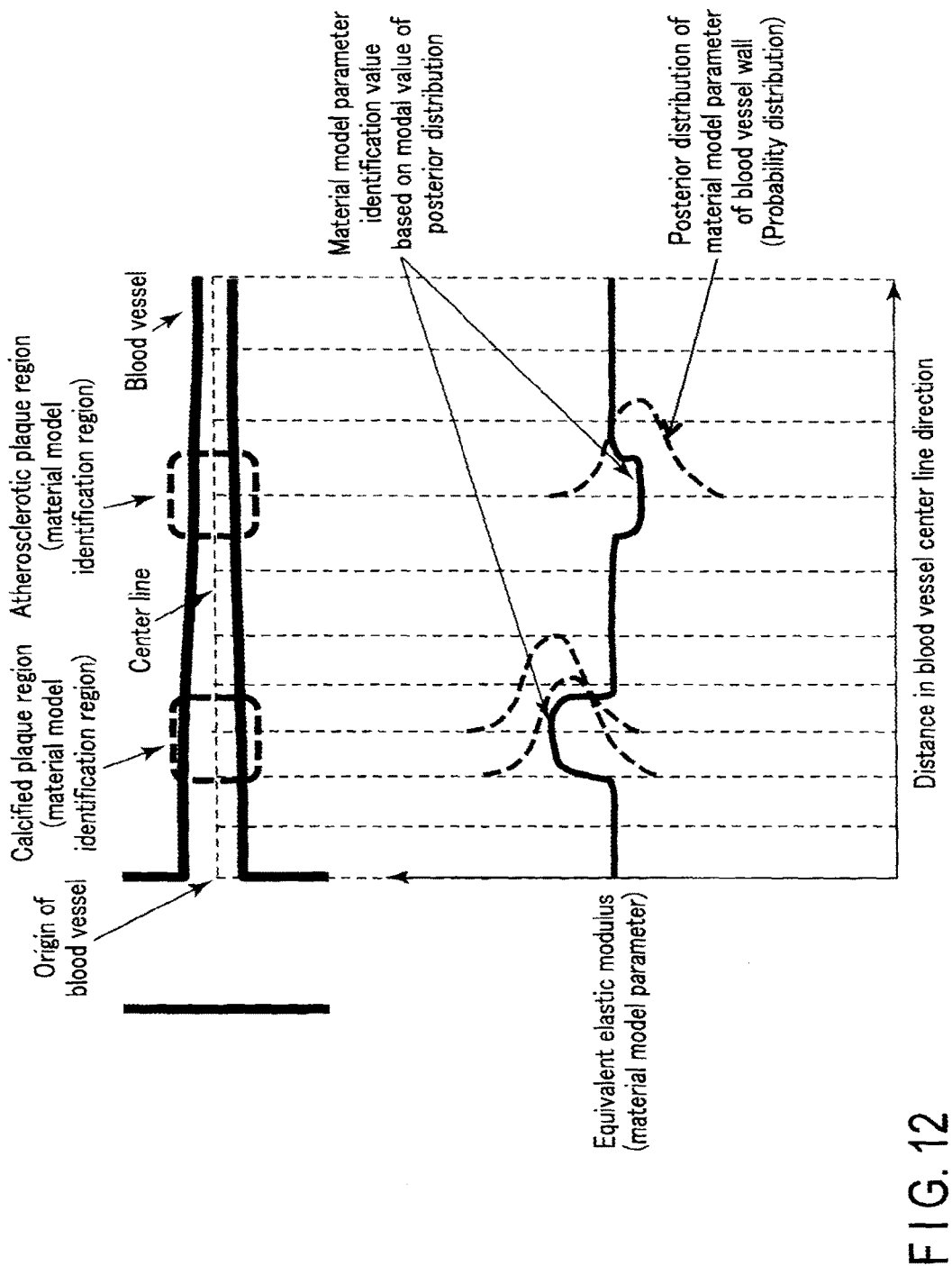
FIG. 12 is a figure for explaining identification of a material model parameter and a posterior distribution calculation about the material model parameter based on hierarchical Bayesian model and Markov chain Monte Carlo method (an equivalent elastic modulus of a blood vessel wall) performed with the statistical identification circuitry of FIG. 4.

FIG. 12 is a figure for explaining the identification of the material model parameter and the posterior distribution calculation about the material model parameter based on hierarchical Bayesian model and Markov chain Monte Carlo method (the equivalent elastic modulus of the blood vessel wall). As shown in FIG. 12, the blood vessel morphology is the same as FIG. 11. The posterior distribution of the parameter of the material model of the blood vessel wall (for example, the equivalent elastic modulus) is calculated by limiting into the material model identification region, and the modal value of the posterior distribution is identified as the identification value. As shown in FIG. 12, the identification value of the material model parameter of the equivalent elastic modulus has a different value according to the calcified plaque region, the atherosclerotic plaque region, and the normal region. In other words, the material can be found by observing the identification value of the material model parameter of the equivalent elastic modulus.

It should be noted that the observation value of the bloodstream index is assumed to be, for example, the volume of blood flow change flown to the aorta, and the observation value of the blood vessel morphology index can be used as the capacity change value (CFA) of the left ventricle measured by the image processing from the time-series CT image. The temporal change of the movement amount of the feature point is calculated by the image tracking of the contrast agent after the contrast agent is injected into the coronary artery, so that the flow rate and the volume of flow may be calculated. The density change amount of the contrast agent in the temporal particular region or the blood vessel center line direction is obtained, and the flow rate and the volume of flow may be calculated from the temporal rate of change of the density change and the value obtained by dividing the density change by the distance interval distance in the center line direction of each region. In the case of MRI, the image tracking of proton is used, and in a case of ultrasonic echo, the volume of flow is calculated by contrast echocardiography and the like.

In each step S6, both of the statistical identification processing with the first statistical identification circuitry 61-1 and the statistical identification processing with the second statistical identification circuitry 61-2 may not be performed. More specifically, in step S6, any one of the statistical identification processing with the first statistical identification circuitry 61-1 and the statistical identification processing with the second statistical identification circuitry 61-2 may be performed.

In the above example, the first statistical identification circuitry 61-1 statistically identifies the parameter of the latent variable so that the prediction value of the blood vessel morphology index is in conformity with the observation value of the blood vessel morphology index, and the second statistical identification circuitry 61-2 statistically identifies the parameter of the latent variable so that the prediction value of the bloodstream index is in conformity with the observation value of the bloodstream index. However, the statistical identification circuitry 61 may statistically identify the parameter of the latent variable based on the structure-fluid interaction analysis so that the prediction value of the blood vessel morphology index and the prediction value of the bloodstream index are in conformity with the observation value of the blood vessel morphology index and the observation value of the bloodstream index.

When step S6 is performed, the system control circuitry 21 causes the image processing circuitry 27 to perform setting processing (step S7). In step S7, the dynamical model structuring circuitry 55 of the image processing circuitry 27 sets the parameter of the latent variable calculated in step S6 to the dynamical model.

When step S7 is performed, the system control circuitry 21 determines whether the identification termination condition is satisfied or not (step S8). When the identification termination condition is determined not to be satisfied in step S8 (step S8: NO), the system control circuitry 21 repeats steps S4, S5, S6, S7 and S8. In this case the identification termination condition is expressed by whether the index for determining the identification termination (hereinafter referred to as an identification termination index) attains the defined value. Examples of identification termination indexes include a difference value between the prediction value and the observation value of the blood vessel morphology index. In this case, when this difference value is more than an already-determined value, the system control circuitry 21 determines that the identification termination condition is not satisfied, and when the difference value is less than the already-determined value, the system control circuitry 21 determines that the identification termination condition is satisfied. For example, the identification termination index may be the number of sampling points of the Monte Carlo method. In this case, when the number of sampling points is less than the already-determined value, the system control circuitry 21 determines that the identification termination condition is not satisfied, and when the number of sampling points is more than the already-determined value, the system control circuitry 21 determines that the identification termination condition is satisfied. When the identification termination condition is determined to be satisfied, the dynamical model structuring circuitry 55 sets the latest dynamical model at that point in time to the ultimate dynamical model.

Steps S4, S5, S6, S7 and S8 explained above may be repeated according to the same identification method, or may be repeated according to different identification methods. When steps S4, S5, S6, and S7 are repeated in accordance with different identification methods, for example, first, a simplified dynamical model may be used to temporarily identify the latent variable, and subsequently, a continuum dynamical model may be used to accurately identify the latent variable. As described above, the statistical identification processing is performed in two steps in accordance with different schemes, and the parameter of the latent variable can be converged in a short time. A method using the simplified dynamical model includes a method using an expression of a material dynamics of a thick cylinder and an expression of Hagen-Poiseuille flow and modified Bernoulli with the internal pressure and the external pressure. A method using a continuum dynamical model includes FEM structural fluid analysis.

When the identification termination condition is determined to be satisfied in step S8 (step S8: YES), the system control circuitry 21 may cause the image analysis/tracking processing unit 53 to perform amending processing (step S9). In step S9, the image analysis/tracking processing unit 53 amends the shape of the blood vessel region included in the time-series medical image so that the structural fluid analysis result carried out based on the latent variable obtained by the inverse analysis according to the statistical identification method (the prediction values of the dynamical index and the prediction value of the blood fluid index) are in conformity with the observation values (the observation value of the dynamical index and the observation value of the blood fluid index). The display 31 displays a diagnosis result based on the amended time-series medical image.

Therefore, the blood vessel analysis apparatus 50 can display the diagnosis result in view of the ultimate dynamical model. Alternatively, the display 31 may display, on a screen, a blood vessel portion/region in which the identification with the inverse analysis and the observation result with the structural fluid analysis are not in conformity.

When step S9 is performed, the system control circuitry 21 causes the image processing circuitry 27 to perform the blood vessel stress analysis processing (step S10). In step S10, the blood vessel stress analysis circuitry 57 of the image processing circuitry 27 performs the blood vessel stress analysis on the ultimate dynamical model, and calculates the space distribution of the prediction value of the time-series dynamical index. More specifically, the prediction value of the dynamical index for each discretized region is calculated.

When step S9 is performed, the system control circuitry 21 causes the image processing circuitry 27 to perform the blood fluid analysis processing (step S11). The blood fluid analysis circuitry 59 of the image processing circuitry 27 in step S11 performs the blood fluid analysis on the dynamical model temporarily structured, and calculates the space distribution of the prediction value of the time-series bloodstream index. More specifically, the prediction value of the bloodstream index for each discretized region is calculated.

It should be noted that the FFR may be calculated as the dynamical index or the bloodstream index.

When steps S10 and S11 are performed, the system control circuitry 21 causes the display 31 to perform the display processing (step S12). In step S12, the display 31 displays the prediction value of the time-series dynamical index calculated in step S10 and the prediction value of the time-series bloodstream calculated in step S11. For example, the display 31 displays the time-series dynamical index or the time-series bloodstream index in a motion picture manner in which the time-series dynamical model is in a color according to the prediction value. Therefore, the display 31 holds a color table indicating a relationship between various kinds of prediction values and color values (for example, RGB). The display 31 uses a color table to identify the color value according to the prediction value, and displays the discretized region corresponding to the prediction value in a color according to the color value identified.

Figure 13:
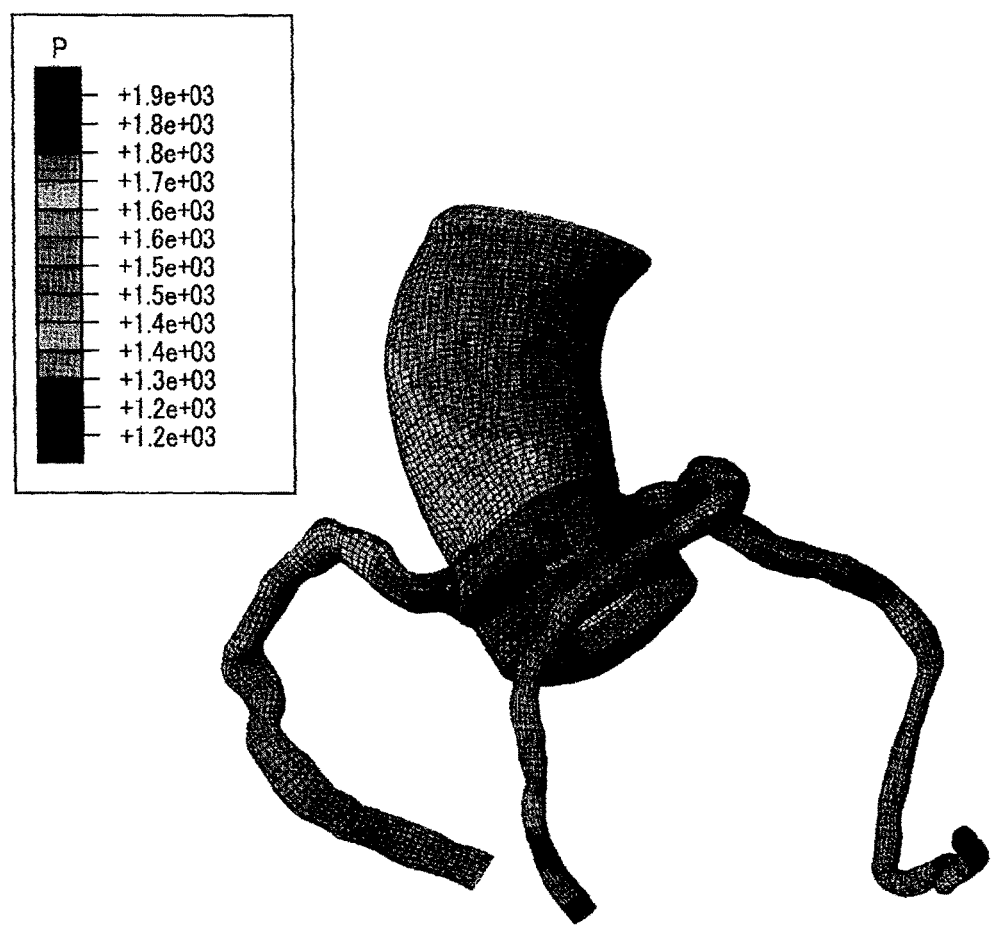
FIG. 13 is a figure illustrating an example of display of a space distribution of an internal pressure which is one of dynamical indexes according to the display device of FIG. 1.

FIG. 13 is a figure illustrating an example of display of a space distribution of an internal pressure which is one of dynamical indexes. As shown in FIG. 13, the display 31 displays each discretized region constituting the dynamical model in a motion picture manner in a color according to the internal pressure value about the discretized region. When the user observes the dynamical model, the user can find, based on the color, the dynamical index changing over time or space.

When step S11 is performed, the structural fluid analysis processing is terminated.

It should be noted that the amending processing in step S9 may not be necessarily performed. When the amending processing is not necessary, step S10 or step S11 may be performed when the identification termination condition is satisfied in step S8.

In the above embodiments, the allocation target of the constraint condition of the forced displacement history is considered to be allocated uniformly to all the nodes. However, the present embodiment is not limited thereto. For example, the allocation target of the constraint condition of the forced displacement history may be divided according to whether the boundary condition and the material model are identified or not. FIGS. 14A and 14B are figures illustrating another example of allocation of forced displacement history, and illustrates a cross section of the shape model. For example, when the boundary condition and the material model are identified as shown in FIG. 14A, the forced displacement history is allocated only to the node PN2 on the external wall unit OW of the shape model, and the forced displacement history is allocated to the node PN3 of the blood vessel wall region RV. When the boundary condition and the material model are identified as shown in FIG. 14B, the forced displacement history is preferably allocated to both of the node PN2 of the external wall unit of the shape model and the node PN3 of the blood vessel wall region RV. In this case, the forced displacement history is allocated to the node PN1 on the center line. The node PN1 and the node PN2 of the external wall unit OW may be connected with the beam element EB, and the forced displacement history may be allocated to the nodes PN2 and PN3 on the beam element EB. At this occasion, the contraction and the expansion in the circle are expressed as the expansion and contraction displacement of the beam element EB. The forced displacement history may not be allocated to the lumen region RI in order to ensure the displacement freedom degree.

FIG. 15 is a figure illustrating another example of allocation of forced displacement history, and illustrates a cross section of the shape model including the dummy element RD of the perivascular tissue. In particular, FIG. 15 shows a case where constraint is given by giving forcible displacement history to nodes of dummy element surface around blood vessel wall (latent variable is identified by referring to not only intravascular lumen shape index but also blood vessel wall shape index (case where boundary condition, material model, and load condition are identified)). As shown in FIG. 15, the dummy element RD is set outside of the blood vessel wall region RV. When the shape model includes the dummy element RD, the node PN4 is set to not only the blood vessel wall region RV but also the dummy element RD. The forced displacement history is also allocated to the node PN4. When the boundary condition and the material model are identified, the dynamical model structuring circuitry 55 allocates the forced displacement history to the node PN 3 included in the blood vessel wall region RV, and when the boundary condition and the material model are not identified, the dynamical model structuring circuitry 55 may not allocate the forced displacement history. When the forced displacement history is allocated to the node PN3, the material model is identified in view of not only the shape index of the lumen region RI but also the shape index of the blood vessel wall region RV.

As described above, the deformation freedom degree of the structural fluid analysis can be suppressed by limiting the allocation target of the constraint condition, and the analysis can be performed in a stable and efficient manner. In a case where a dummy element is provided, and the load with the internal pressure affects deformation outside of the center line longitudinal cross section, the load vector applied to the blood vessel and the internal pressure can be separated and the latent variable can be identified in view of the morphology indexes of not only the intravascular lumen but also the blood vessel wall. Cases where the load given by the internal pressure affects deformation outside of the center line longitudinal cross section includes a case where there is a protrusion on the intravascular lumen and the blood vessel branching portion and the like. A dummy element set simulates a fat layer of a wall surface in terms of physiology. On the other hand, in the numerical calculation, a forced displacement is given to the blood vessel wall surface with the dummy element set, so that there is an effect of avoiding generation of a stress different from the reality in a local portion in the blood vessel wall.

FIG. 16 is a figure illustrating another example of allocation of forced displacement history, and illustrates a cross section of the shape model including the plaque region RP. In particular, in FIG. 16, latent variables of plaque and blood vessel wall are respectively identified by referring to not only intravascular lumen shape index but also blood vessel wall shape index and plaque shape index (case where boundary condition, material model, and load condition are identified). As shown in FIG. 16, the plaque region RP is included in the blood vessel wall region RV. The plaque region RP is set in the material model identification region. For the plaque region RP, the material model is identified in view of the lumen shape index, the blood vessel wall shape index, and the plaque index (CT value). The dynamical model structuring circuitry 55 divides the plaque region into multiple partial regions in accordance with the property. For example, the dynamical model structuring circuitry 55 sets multiple local regions in the plaque region, and identifies the material model parameter of each local region by using the CT value—material model table from the CT values of multiple pixels included in each local region. Then, the dynamical model structuring circuitry 55 sets the identified material model parameter (or, the parameter range) in the local region. Then, in each partial region, the parameter range according to the property of the partial region is preferably set in advance. With the statistical identification processing explained above, the material model parameter for each partial region is identified by the statistical identification circuitry 61. Then, in step S12, the display 31 displays the index about the material characteristics of the blood vessel as the dynamical index, so that the user can accurately and easily find the property of the plaque.

As shown in FIG. 16, the dynamical model structuring circuitry 55 may configure such that the calculation density of the attention-given region such as a plaque region in the dynamical model is higher than the calculation density of another region. It should be noted that configuring the calculation density of the attention-given region to be higher than another region also includes configuring the calculation density of the another region to be lower than the calculation density of the attention-given region. The calculation density can be adjusted according to the density of a lattice and a calculation element such as a node. It should be noted that the dynamical model structuring circuitry 55 can set the attention-given region at any given location in accordance with a command given with the input device 29 by the user. The calculation density of the attention-given region is configured to be higher than another region, so that precise structural fluid analysis can be performed by applying limitation into the attention-given region while preventing the processing efficiency from being reduced. In addition, the calculation density in an region other than the attention-given region is configured to be lower than the calculation density of the attention-given region, so that the calculation speed can be improved while the precision of the structural fluid analysis can be maintained with regard to the attention-given region. It should be noted that the attention-given region is not limited to the plaque region, and can be set in any given region with the input device 29 by the user.

As described above, the blood vessel analysis apparatus 50 according to the present embodiment includes the storage 33, the dynamical model structuring circuitry 55, the statistical identification circuitry 61, and the analysis circuitrys 57, 59. The storage 33 stores data of time-series medical images of blood vessels of a subject. The dynamical model structuring circuitry 55 temporarily structures the dynamical model of the analysis processing based on the time-series medical images. The statistical identification circuitry 61 identifies the latent variable of the latent variable identification region so that at least one of the prediction value of the blood vessel morphology index and the prediction value of the bloodstream index based on the temporarily structured dynamical model is in conformity with at least one of the observation value of the blood vessel morphology index and the observation value of the blood vessel morphology index measured in advance. The analysis circuitrys 57, 59 applies the analysis processing to the dynamical model to which the identified latent variable is allocated.

According to the above configuration, the blood vessel analysis apparatus 50 according to the present embodiment can identify the latent variable such as material model, boundary condition, load condition, and geometric structure, and the like by performing inverse analysis using the blood vessel shape deformation index and the bloodstream index. The blood vessel analysis apparatus 50 repeatedly performs the inverse analysis while changing the latent variable, so that the blood vessel analysis apparatus 50 can identify the latent variable in view of all of the four difficulties explained above, i.e., 1. the identification method of the material model of the coronary artery, 2. incorporation of the effect of the deformation of the shape of the heart to the coronary artery, 3. the identification method of the boundary condition of the coronary artery, and 4. the identification method of the load condition and the boundary condition and the material model using the blood vessel shape having uncertainty. Therefore, the blood vessel analysis apparatus 50 can execute the structural fluid analysis in view of the effect of the external factor such as the blood vessel, the heart, and the like that are not drawn in a CT image.

In the CT scan, stress such as vasodilator drug is given to a subject in order to enhance drawing performance and the like of blood vessel. When the vasodilator drug is injected into the subject, the blood vessel of the subject expands, and the blood vessel region included in the CT image becomes clear. However, the vasodilator drug causes arteriosclerosis in the blood vessel. In a case where the CT scan is executed under the stress, and time-series CT images (hereinafter referred to as stress-applied CT image) are collected, parameters of latent variables such as a boundary condition, a load condition, and the like and the material model are identified by using the time-series stress-applied CT images. However, the parameter of the latent variable based on the stress-applied CT image may be different from the parameter of the latent variable based on the heart blood vessel of the subject in normal circumstances (stress-less situation) in which no stress is applied.

The blood vessel analysis apparatus 50 according to the present embodiment makes the parameter of the latent variable to be closer to the parameter of the stress-less situation, so that the time-series CT image collected by the CT scan in the stress-less situation (hereinafter referred to as a stress-less image) is used as the time-series CT image of the analysis target. The blood vessel analysis apparatus 50 may identify parameters of latent variables such as a boundary condition, a load condition, and the like and the material model based on the time-series stress-less image. In addition, The blood vessel analysis apparatus 50 makes the parameter of the latent variable based on the stress-applied CT image to be closer to the parameter of the stress-less situation, and therefore, correction can be done by using the stress-less image. As described above, the stress-applied CT image is used, so that the parameter of the latent variable can be made to be closer to the parameter in normal circumstances, and more accurate blood vessel structure analysis can be performed.

As described above, according to the present embodiment, the precision of the structural fluid analysis of the blood vessel can be improved.

Application Example

A blood vessel analysis apparatus 50 according to an application example determines whether collateral exists or not by using the dynamical index calculated based on the dynamical model.

FIGS. 17A and 17B are figures for explaining collateral. FIG. 17A is a schematic diagram of a heart where collateral does not exist. FIG. 17B is a schematic diagram of a heart where collateral exists. As shown in FIG. 17A, in a case where the blood vessel is closed due to stenosis, thrombus, and the like, blood does not flow in the blood vessel at the downstream of the obstruction existing portion RS, and no blood spreads to the dominating region of the blood vessel. Therefore, the tissue in the dominating region is necrotized. In order to allow the blood to spread into the dominating region, a detour circuit to the dominating region is formed as shown in FIG. 17B. This detour circuit is a microvessel called a collateral RC. With the collateral RC, blood stream in the blood vessel at the downstream of the obstruction portion to the dominating region is ensured, and the perfusion to the heart is maintained. With the collateral, the necrosis region RN is reduced. The collateral is very small, and normally, the collateral is not drawn in the CT image. Therefore, in a case where there is a collateral, the behavior with the collateral cannot be completely reflected in the dynamical model based on the blood vessel region drawn in the CT image, and the accuracy of the dynamical model is degraded.

The image processing circuitry 27 according to the application example determines whether there is collateral or not, and therefore, the image processing circuitry 27 further includes a collateral determination circuitry 63 as shown in FIG. 4. The image processing circuitry 27 according to the application example can restructure the dynamical model in view of the existence of the collateral.

The details of processing according to the application example will be hereinafter explained. FIG. 18 is a figure illustrating a typical flow of processing performed under the control of the system control circuitry 21 according to the application example.

For example, the system control circuitry 21 starts processing according to the application example as shown in FIG. 18 upon receiving a determination start command for determining whether collateral exists or not. For example, this determination start command is preferably automatically issued after step S9 of FIG. 3 (in a case where the identification termination condition is determined to be satisfied in step S8 in a case where step S9 is not performed). The determination start command may be input with the input device 29 by the user any given point in time after the dynamical model is structured. In this case, it is considered that the storage 33 is storing a dynamical model structured by the processing of FIG. 3 explained above.

Upon receiving a determination start command, the system control circuitry 21 causes the image processing circuitry 27 to perform the blood fluid analysis processing (step S21). According to the same method as step S10, the blood vessel stress analysis circuitry 57 of the image processing circuitry 27 in step S21 performs the blood vessel stress analysis on the dynamical model structuring circuitry, and calculates the space distribution of the prediction value of the dynamical index. In a case where the determination start command is input with the input device 29 by the user, the blood vessel stress analysis circuitry 57 reads the dynamical model from the storage 33, and calculates the space distribution of the prediction value of the dynamical index based on the read dynamical model. The index affected by whether the collateral exists or not is employed as the dynamical index calculated in step S21. More specifically, dynamical indexes calculated in step S21 include the internal pressure, the stress, the distortion, and the like.

When step S21 is performed, the system control circuitry 21 causes the image processing circuitry 27 to perform the determination processing (step S22). In step S22, the collateral determination circuitry 63 of the image processing circuitry 27 determines whether there is collateral or not based on the change mode of the prediction value of the time-series dynamical index in the center line direction.

Figure 19:
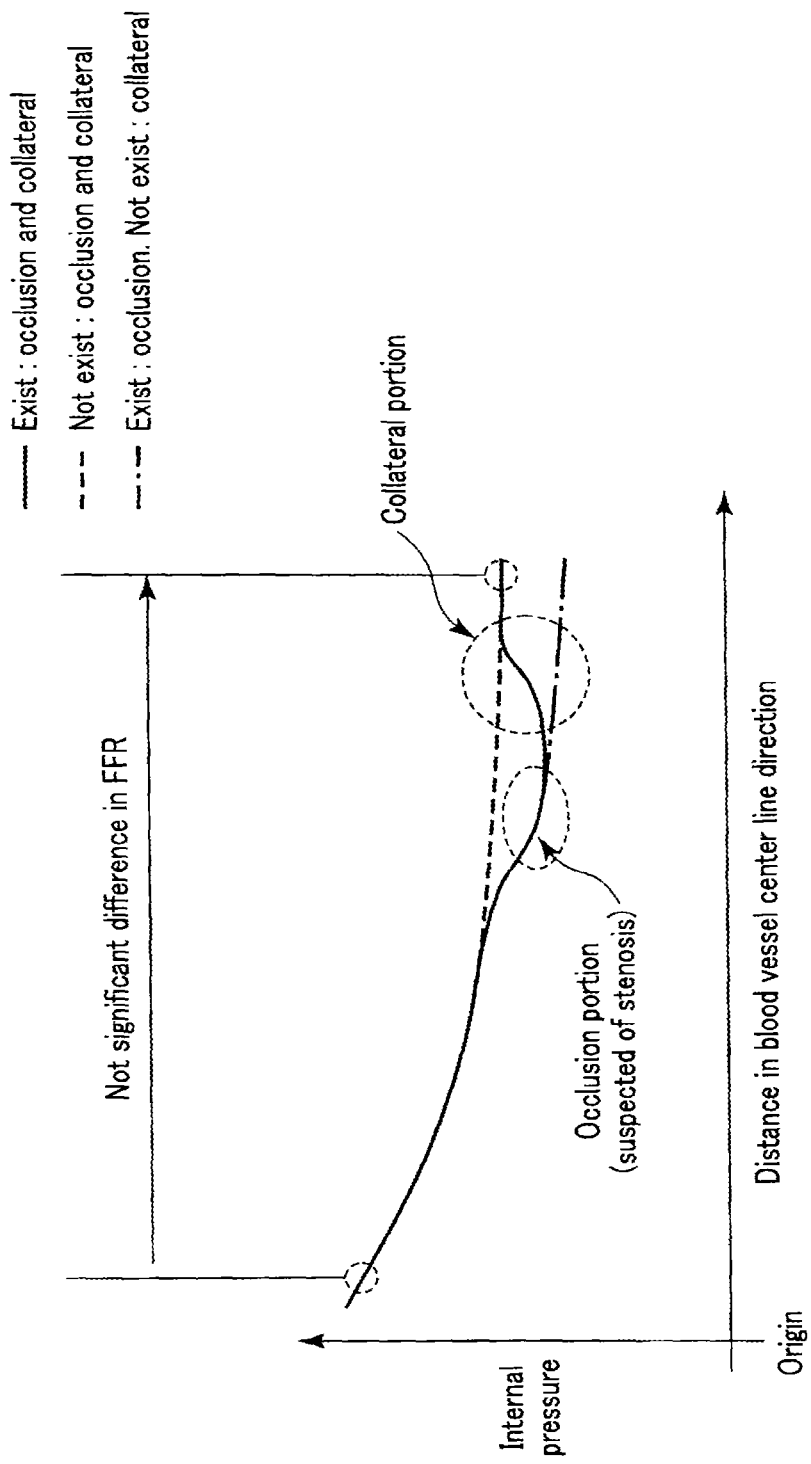
FIG. 19 is a figure for explaining determination processing in which a collateral determination circuitry of an image processing circuitry according to an application example of the present embodiment determines whether collateral exists or not.

FIG. 19 is a figure for explaining determination processing in which the collateral determination circuitry 63 determines whether there is collateral or not. FIG. 19 illustrates a graph illustrating a space distribution of an internal pressure. The vertical axis of the graph of FIG. 19 is defined as an internal pressure which is one of the dynamical indexes, and the horizontal axis is defined as a blood vessel center line direction distance from the blood vessel origin. As shown in FIG. 19, in a case where there is not any obstruction due to stenosis, thrombus, and the like (dotted line of FIG. 19), the internal pressure gradually decreases as the distance from the origin increases. When obstruction exists, the internal pressure rapidly decreases at the obstruction existing portion. In a case where obstruction exists, and no collateral exists (broken line in FIG. 19), the internal pressure that has rapidly decreased at the obstruction existing portion is still at a low level even if the distance from the origin further increases. However, in a case where obstruction exists, and collateral exists (alternate long and short dashed line FIG. 19), the internal pressure that has rapidly decreased in the obstruction existing portion increases again in the portion where the collateral exists. As described above, in a case where collateral exists, the space distribution of the internal pressure indicates a peculiar change mode. For example, in a case of FFR measurement using a catheter, an FFR value is measured based on the internal pressure difference of two points. Therefore, in a case where the internal pressures at two points sandwiching the portion where the collateral exists are measured, the FFR value based on the internal pressures of the two points cannot reflect the existence of the collateral.

The collateral determination circuitry 63 determines whether collateral exists or not by using a peculiar change mode of the space distribution of the internal pressure value indicated in a case where collateral exists. More specifically, the collateral determination circuitry 63 analyzes the shape in the change curved line of the internal pressure value along the distance from the origin, and after the internal pressure value once rapidly decreases as the distance from the origin increases, the collateral determination circuitry 63 determines whether the internal pressure value turns to increase or not. For example, the collateral determination circuitry 63 calculates the distance differential value of the internal pressure value with a regular distance, and in a case where the distance differential value of the internal pressure value is equal to or less than a threshold value (hereinafter referred to as a decrease threshold value), the internal pressure value is determined to have rapidly decreased. In a case where the distance differential value of the internal pressure value is determined to be less than the decrease threshold value, the collateral determination circuitry 63 sets the position in the obstruction existing portion. The collateral determination circuitry 63 calculates the distance differential value of the internal pressure value from the obstruction existing portion with a regular distance interval, and in a case where the distance differential value of the internal pressure value is equal to or more than a threshold value (hereinafter referred to as an increase threshold value), the internal pressure value is determined to have increased. In a case where the distance differential value of the internal pressure value is determined to be more than the increase threshold value, the collateral determination circuitry 63 determines that the collateral exists. In a case where the distance differential value of the internal pressure value is determined to be more than the increase threshold value, the collateral determination circuitry 63 sets the position in the portion where collateral exists. It should be noted that the decrease threshold value the increase threshold value explained above can be set separately from any given value. As described above, in a case where the internal pressure value once rapidly decreases, and turns to increase, the collateral determination circuitry 63 determines that collateral exists, and in a case where the internal pressure value indicates another change mode, the collateral determination circuitry 63 determines that no collateral exists. The internal pressure is explained as an example of a dynamical index in order to explain determination processing of collateral performed by the collateral determination circuitry 63 in a more specific manner, but the dynamical index that can be used for the determination processing of the collateral is not limited to the internal pressure. For example, not only the internal pressure but also stress, distortion, and the like can be used in the same manner for the determination processing of the collateral.

When step S22 is performed, the system control circuitry 21 causes the display 31 to perform the display processing (step S23). In step S23, the display 31 displays the determination result indicating whether collateral exists or not given by the collateral determination circuitry 63 in step S22. More specifically, in a case where the collateral determination circuitry 63 determines that collateral exists, the display 31 displays a message to that effect, and in a case where the collateral determination circuitry 63 determines that no collateral exists, the display 31 displays a message to that effect. In a case where collateral is determined to exist, the display 31 may clearly indicate a portion where the collateral exists on the graph of FIG. 19 and the dynamical model. Further, the display 31 may clearly indicate an obstruction portion of stenosis, thrombus, and the like on the graph of FIG. 19 and the dynamical model.

When step S23 is performed, the system control circuitry 21 determines whether the system control circuitry 21 performs identification of the latent variable again or not (step S24). For example, in a case where the collateral is determined to exist, the system control circuitry 21 determines to automatically perform identification of the latent variable again in step S24, and in a case where the collateral is determined not to exist, the system control circuitry 21 determines not to automatically perform identification of the latent variable again. In a case where a command for performing the perform identification again is given with the input device 29 by the user, it may be determined to perform the identification of the latent variable again, and in a case where the command is not given with the input device 29, it may be determined not to perform the identification of the latent variable again. In this case, the user refers to the determination result as to whether the collateral exists or not, and determines whether it is necessary to perform the identification of the latent variable again or not. For example, the user observes a CT image, and in a case where the collateral is determined to be likely to exist, it is determined that it is necessary to perform the identification of the latent variable again. In a case where it is determined that it is necessary to perform the identification of the latent variable again, the user inputs a command for performing the identification of the latent variable again with the input device 29.

In a case where it is determined that the identification of the latent variable is not performed again in step S24 (step S23: NO), the system control circuitry 21 terminates the processing according to the application example.

In a case where the identification of the latent variable is determined not to be performed again in step S24 (step S23: YES), the system control circuitry 21 causes the image processing circuitry 27 to perform the setting processing (step S25). In step S25, the dynamical model structuring circuitry 55 of the image processing circuitry 27 sets, in the dynamical model, a boundary condition in view of the existence of the collateral. For example, dynamical model structuring circuitry 55 sets, in a portion where the collateral exists, the initial value of the boundary condition about the flow in and flow out of the blood with the collateral. A value in a range empirically defined may be used as necessary as the initial value of the flow in and flow out condition.

When the boundary condition in view of the existence of the collateral is set, the system control circuitry 21 repeatedly performs steps S4, S5, S6, S7, and S8, and determines the parameters of the latent variables of the dynamical model in view of the existence of the collateral. After the parameters of the latent variables are determined in step S9, amending of the medical image analysis/image tracking processing and display of the amending result are performed, and the time-series dynamical index is calculated based on the dynamical model in step S10, and the time-series bloodstream index is calculated based on the dynamical model in step S11, and the time-series dynamical index and the time-series bloodstream index are displayed in step S12. These steps S4, S5, S6, S7, S8, S9, S10, S11, and S12 are the same as the processing as shown in FIG. 3, and therefore they are not explained repeatedly.

The explanation about the processing according to the application example has been hereinabove explained.

According to the application example, whether there is collateral that is not drawn on the CT image can be determined by using the dynamical model. Then, an accurate dynamical model in view of the existence of the collateral can be structured by re-identifying the parameters of the latent variables in view of the existence of the collateral by using the inverse analysis.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A blood vessel analysis apparatus, comprising:
a memory to store data of a medical image of a blood vessel of a subject; and
processing circuitry configured to
calculate a blood flow index which is related to blood pressure along the blood vessel based on the data of the medical image,
determine whether a collateral vessel exists or not, based on a change mode of the blood flow index along the blood vessel, the change mode being a mode in which the blood flow index at a first position is higher than the blood flow index at a second position, the first position being located in a distal side of the second position along the blood vessel, and
output a determination result,
wherein the first and second positions, which are used by the processing circuitry to determine whether the collateral blood vessel exists or not, are located in an identical coronary artery.

2. The apparatus according to claim 1, wherein the processing circuitry is further configured to determine whether the collateral vessel exists or not, based on the change mode of the blood flow index along the blood vessel, the change mode being a mode in which the blood flow index at a third position is lower than the blood flow index at the first position and the blood flow index at the second position, the third position being located between the first position and the second position along with the blood vessel.

3. The apparatus according to claim 2, wherein the blood flow index at the third position is a minimum of the blood flow index along the blood vessel.

4. The apparatus according to claim 1, wherein the processing circuitry is further configured to calculate a time-series blood flow index along the blood vessel, based on a time-series medical image, and determine whether the collateral vessel exists or not based on a change mode of the time-series blood flow index.

5. The apparatus according to claim 4, wherein the processing circuitry is further configured to
temporarily structure a dynamical model of analysis processing based on the time-series medical image,
identify a latent variable of the dynamical model so that at least one of a prediction value of a blood vessel morphology and a prediction value of a bloodstream based on the temporarily structured dynamical model is in conformity with at least one of an observation value of the blood vessel morphology and an observation value of the bloodstream measured in advance, and
analyze the dynamical model to which the identified latent variable is allocated.

6. The apparatus according to claim 5, wherein the processing circuitry is further configured to
perform structure analysis, fluid analysis, or structural fluid interaction analysis with the dynamical model to which the identified latent variable is allocated, and
calculate at least one of a prediction value of the time-series dynamical index and a prediction value of the time-series bloodstream.

7. The apparatus according to claim 5, wherein the processing circuitry is further configured to identify the latent variable of the dynamical model so that the prediction value of the blood vessel morphology and the prediction value of the bloodstream are in conformity with the observation value of the blood vessel morphology and the observation value of the bloodstream.

8. The apparatus according to claim 4, wherein the processing circuitry is further configured to set an analysis target region in a blood vessel region included in the time-series medical image, and set a latent variable identification region in the analysis target region, calculate a time-series morphology index and a time-series shape deformation index of the analysis target region by performing image processing of the time-series medical image, and temporarily structure a dynamical model of analysis processing of the analysis target region, based on the time-series morphology index, the time-series shape deformation index, and the time-series medical image.

9. The apparatus according to claim 8, wherein the processing circuitry is further configured to locally set the analysis target region to a lesion region or a treatment target.

10. The apparatus according to claim 8, wherein the processing circuitry is further configured to locally set the analysis target region to a blood vessel region where a diameter is equal to or more than 2 mm.

11. The apparatus according to claim 8, wherein the processing circuitry is further configured to exclude a pixel region of a blood vessel in a heart from the analysis target region.

12. The apparatus according to claim 4, wherein the memory further stores each of a plurality of CT value ranges in association with a property of a blood vessel wall and a material model, wherein the latent variable includes the material model, the time-series medical image is a time-series CT image generated by an X-ray computed tomography apparatus, and the processing circuitry is further configured to identify the material model associated in the memory with a CT value of a pixel constituting a blood vessel wall region included in the medical image, and allocate the identified material model to the blood vessel wall region of the dynamical model.

13. The apparatus according to claim 4, wherein the latent variable includes a boundary condition related to a blood flow inlet and a blood flow outlet, and the processing circuitry is further configured to calculate an initial value of the boundary condition based on the time-series CT image generated by a CT scan for a subject injected with a contrast agent, by an X-ray computed tomography apparatus.

14. The apparatus according to claim 4, wherein the processing circuitry is further configured to set a higher calculation density to an interest region in the dynamical model than another region.

15. The apparatus according to claim 4, wherein the time-series medical image is a time-series CT image generated by an X-ray computed tomography apparatus, and the X-ray computed tomography apparatus executes a CT scan so that a temporal resolution of a designation section in the time-series CT image is higher than a temporal resolution of another section.

16. The apparatus according to claim 4, wherein the time-series medical image is a time-series CT image generated by an X-ray computed tomography apparatus when the subject is in a stress-less situation.

17. The blood vessel analysis apparatus of claim 1, wherein the processing circuitry is further configured to output the result, which indicates whether the collateral vessel exists or not.

18. A blood vessel analysis method comprising:
acquiring data of a medical image of a blood vessel of a subject;
calculating, by processing circuitry, a blood flow index which is related to blood pressure along the blood vessel based on the data of the medical image,
determining, by the processing circuitry, whether a collateral vessel exists or not, based on a change mode of the blood flow index along the blood vessel, the change mode being a mode in which the blood flow index at a first position is higher than the blood flow index at a second position, the first position being located in a distal side of the second position along the blood vessel, and
outputting a determination result,
wherein the first and second positions, which are used by the processing circuitry to determine whether the collateral blood vessel exists or not, are located in an identical coronary artery.

19. A non-transitory computer-readable medium storing a program causing a computer to perform a process, the process comprising;
acquiring data of a medical image of a blood vessel of a subject;
calculating a blood flow index which is related to blood pressure along the blood vessel based on the data of the medical image,
determining whether a collateral vessel exists or not, based on a change mode of the blood flow index along the blood vessel, the change mode being a mode in which the blood flow index at a first position is higher than the blood flow index at a second position, the first position being located in a distal side of the second position along the blood vessel, and
outputting a determination result,
wherein the first and second positions, which are used to determine whether the collateral blood vessel exists or not, are located in an identical coronary artery.

* * * * *